Figure 1:
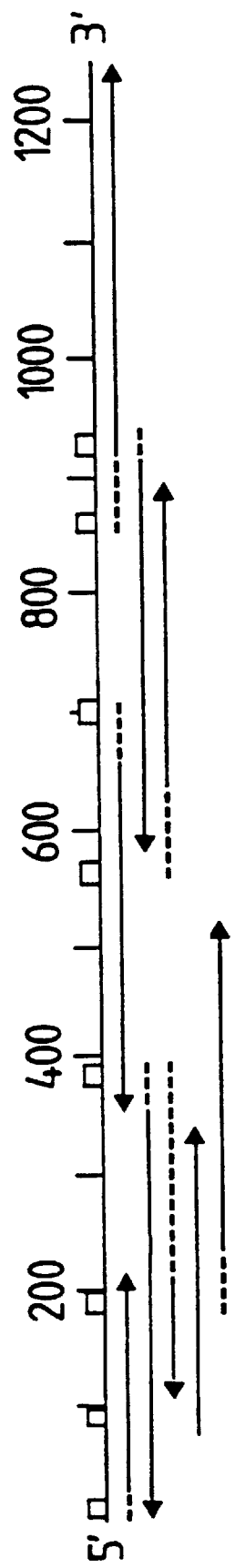

United States Patent [19]
Content et al.

[11] Patent Number: 5,955,356
[45] Date of Patent: Sep. 21, 1999

[54] NUCLEIC ACIDS, VECTORS, AND HOST CELLS INCLUDING MYCOBACTERIUM DERIVED SEQUENCES

[75] Inventors: Jean Content, Rhode St-Genes; Lucas De Wit, Puurs; Jacqueline De Bruyn, Beersel, all of Belgium

[73] Assignee: N.V. Innogenetics S.A., Ghent, Belgium

[21] Appl. No.: 08/107,676

[22] PCT Filed: Feb. 7, 1992

[86] PCT No.: PCT/EP92/00268

§ 371 Date: Oct. 4, 1993

§ 102(e) Date: Oct. 4, 1993

[87] PCT Pub. No.: WO92/14823

PCT Pub. Date: Sep. 3, 1992

[30] Foreign Application Priority Data

Feb. 14, 1991 [EP] European Pat. Off. .............. 91400388

[51] Int. Cl.⁶ .............................. C12N 5/00; C12N 1/20; C12N 15/00; C07H 21/04

[52] U.S. Cl. ...................... 435/325; 435/358; 435/365; 435/252.3; 435/252.33; 435/254.11; 435/320.1; 435/69.3; 536/23.7

[58] Field of Search ................................. 536/27.3, 23.7; 435/69.3, 320.1, 252.3, 252.33, 325, 358, 365, 254.11

[56] References Cited

FOREIGN PATENT DOCUMENTS

WO 87/01118  2/1987  WIPO .
WO 90/10701  9/1990  WIPO .
WO 90/12875  11/1990  WIPO .

OTHER PUBLICATIONS

Parsons, J.A. (ed) "Peptide Hormones", published by University Park Press (Baltimore), see Chapter 1 by Rudinger, E.J., "Characteristics of the amino acids as components of a peptide hormone sequence", pp. 1–7, Jun. 1976.

Lazar et al. Mol. Cell. Biol. 8(3):1247–52 Mar. 1988.

Kumar et al. PNAS 87:1337–1341 1990.

Bowie et al. Science 247:1306–1310 1990.

Shinnick, "The 65–Kilodalton Antigen of Mycobacterium tuberculosis", *Journal of Bacteriology*, 169:1080–1088 (Mar. 1987).

Matsuo et al., "Cloning and Expression of the Gene for the Cross–Reactive α–Antigen of *Mycobacterium kansasii* ", *Infection and Immunity*, 58:550–556 (Feb. 1990).

Nagai et al., "Isolation and Partial Characterization of Major Protein Antigens in the Culture Fluid of Mycobacterium tuberculosis", *Infection and Immunity*, 59:372–382 (Jan. 1991).

Wiker et al., "Evidence for Three Separate Genes Encoding the Proteins of the Mycobacterial Antigen 85 Complex", *Infection and Immunity*, vol. 58, No. 1, pp. 272–274 (Jan. 1990).

Worsaae et al., "Allergenic and Blastogenic Reactivity of Three Antigens from Mycobacterium tuberculosis in Sensitized Guinea Pigs", *Infection and Immunity*, vol. 55, pp. 2922–2927 (Dec. 1987).

*Primary Examiner*—Anthony C. Caputa
*Assistant Examiner*—Mark Navarro
*Attorney, Agent, or Firm*—Merchant, Gould, Smith, Edell, Welter & Schmidt, P.A.

[57] ABSTRACT

The invention relates to nucleic acids which contain particularly a nucleotide sequence extending from the extremity constituted by the nucleotide at position (1) to the extremity constituted by the nucleotide at position (1211) represented on the figure, to the polypeptides coded by said nucleic acids. The polypeptides of the invention can be used for the diagnosis of tuberculosis, and can also be part of the active principle in the preparation of a vaccine against tuberculosis.

11 Claims, 25 Drawing Sheets

```
AGGTGTCCGG GCCGACGCTG AATCGTTAGC CAACCGCGAT    40

CTCGCGCTGC GGCCACGACA TTCGAACTGA GCGTCCTCGG    80

TGTGTTTCAC TCGCCCAGAA CAGATTCGAC CGCGTCGTGC   120

GCAGATGAGA GTTGGGATTG GTAGTAGCT ATG ACG TTC   158
                                 Met Thr Phe
                                  -46

TTC GAA CAG GTG CGA AGG TTG CGG AGC GCA GCG   191
Phe Glu Gln Val Arg Arg Leu Arg Ser Ala Ala
         -40                     -35

ACA ACC CTG CCG CGC CGC GTG GCT ATC GCG GCT   224
Thr Thr Leu Pro Arg Arg Val Ala Ile Ala Ala
         -30                     -25

ATG GGG GCT GTC CTG GTT TAC GGT CTG GTC GGT   257
Met Gly Ala Val Leu Val Tyr Gly Leu Val Gly
         -20                     -15

ACC TTC GGC GGG CCG GCC ACC GCG GGC GCA TTC   290
Thr Phe Gly Gly Pro Ala Thr Ala Gly Ala Phe
 -10                  -5                 -1  1

TCT AGG CCC GGT CTT CCA GTG GAA TAT CTG CAG   323
Ser Arg Pro Gly Leu Pro Val Glu Tyr Leu Gln
         5                       10
```

FIG. I (CONT.)

```
GTG CCA TCC GCG TCG ATG GGC CGC GAC ATC AAG    356
Val Pro Ser Ala Ser Met Gly Arg Asp Ile Lys
            15                  20

GTC CAG TTC CAG GGC GGC GGA CCG CAC GCG GTC    389
Val Gln Phe Gln Gly Gly Gly Pro His Ala Val
            25                  30

TAC CTG CTC GAC GGT CTG CGG GCC CAG GAT GAC    422
Tyr Leu Leu Asp Gly Leu Arg Ala Gln Asp Asp
35                      35                  40

TAC AAC GGC TGG GAC ATC AAC ACC CCG GCC TTC    455
Tyr Asn Gly Trp Asp Ile Asn Thr Pro Ala Phe
                    45                  50

GAG GAG TAC TAC CAG TCA GGG TTG TCG GTG ATC    488
Glu Glu Tyr Tyr Gln Ser Gly Leu Ser Val Ile
                55                  60

ATG CCC GTG GGC GGC CAA TCC AGT TTC TAC ACC    521
Met Pro Val Gly Gly Gln Ser Ser Phe Tyr Thr
            65                  70

GAC TGG TAT CAG CCC TCG CAG AGC AAC GGC CAG    554
Asp Trp Tyr Gln Pro Ser Gln Ser Asn Gly Gln
        75                  80
```

FIG. I (CONT.)

```
AAC TAC ACC TAC AAG TGG GAG ACC TTC CTT ACC   587
Asn Tyr Thr Tyr Lys Trp Glu Thr Phe Leu Thr
 85              90                  95

AGA GAG ATG CCC GCC TGG CTA CAG GCC AAC AAG   620
Arg Glu Met Pro Ala Trp Leu Gln Ala Asn Lys
                100                 105

GGC GTG TCC CCG ACA GGC AAC GCG GCG GTG GGT   653
Gly Val Ser Pro Thr Gly Asn Ala Ala Val Gly
            110                     120

CTT TCG ATG TCG GGC GGT TCC GCG CTG ATC CTG   686
Leu Ser Met Ser Gly Gly Ser Ala Leu Ile Leu
        125                 130

GCC GCG TAC TAC CCG CAG CAG TTC CCG TAC GCC   719
Ala Ala Tyr Tyr Pro Gln Gln Phe Pro Tyr Ala
        135                 140

GCG TCG TTG TCG GGC TTC CTC AAC CCG TCC GAG   752
Ala Ser Leu Ser Gly Phe Leu Asn Pro Ser Glu
145             150                 155

GGC TGG TGG CCG ACG CTG ATC GGC CTG GCG ATG   785
Gly Trp Trp Pro Thr Leu Ile Gly Leu Ala Met
                160                 165

AAC GAC TCG GGC GGT TAC AAC GCC AAC AGC ATG   818
Asn Asp Ser Gly Gly Tyr Asn Ala Asn Ser Met
            170                 175
```

FIG. I (CONT.)

```
TGG GGT CCG TCC AGC GAC CCG GCC TGG AAG CGC    851
Trp Gly Pro Ser Ser Asp Pro Ala Trp Lys Arg
        180                 185

AAC GAC CCA ATG GTT CAG ATT CCC CGC CTG GTC    884
Asn Asp Pro Met Val Gln Ile Pro Arg Leu Val
        190                 195

GCC AAC AAC ACC CGG ATC TGG GTG TAC TGC GGT    917
Ala Asn Asn Thr Arg Ile Trp Val Tyr Cys Gly
200                 205                 210

AAC GGC ACA CCC AGC GAC CTC GGC GGC GAC AAC    950
Asn Gly Thr Pro Ser Asp Leu Gly Gly Asp Asn
                215                 220

ATA CCG GCG AAG TTC CTG GAA GGC CTC ACC CTG    983
Ile Pro Ala Lys Phe Leu Glu Gly Leu Thr Leu
        225                 230

CGC ACC AAC CAG ACC TTC CGG GAC ACC TAC GCG   1016
Arg Thr Asn Gln Thr Phe Arg Asp Thr Tyr Ala
        235                 240

GCC GAC GGT GGA CGC AAC GGG GTG TTT AAC TTC   1049
Ala Asp Gly Gly Arg Asn Gly Val Phe Asn Phe
245                 250

CCG CCC AAC GGA ACA CAC TCG TGG CCC TAC TGG   1082
Pro Pro Asn Gly Thr His Ser Trp Pro Tyr Trp
255                 260                 265
```

FIG. 1 (CONT.)

```
AAC GAG CAG CTG GTC GCC ATG AAG GCC GAT ATC   1115
Asn Glu Gln Leu Val Ala Met Lys Ala Asp Ile
                270             275

CAG CAT GTG CTC AAC GGC GCG ACA CCC CCG GCC   1148
Gln His Val Leu Asn Gly Ala Thr Pro Pro Ala
                280             285

GCC CCT GCT GCG CCG GCC GCC TGA GCCAGCAAGC    1182
Ala Pro Ala Ala Pro Ala Ala TER
                290

CAGCATCGGC AGCAGCGCAA CGGCCAGCG               1211
```

FIG. I (CONT.)

```
                     10           20           30          40
                     *            *            *           *
85A-TUB    TGACCGGCACCGGCGATACGTTGCGGCAGGCATCTGGGCTGGCGG-TGGTT
85B-BCG    ----------------------------------------------------
85B-KAN    ----.TT.--A.T..T.T...TAC.--...TC.CC..C...C...CC.TC.G
85C-TUB    ----------------------------------...TG...C....C-...---
85C-BCG    ----------------------------------------------------

50           60           70          80           90
                     *            *            *           *            *
85A-TUB    CGCCGCTCCGAAGCCCGTCGAACACCATCGCCAGCGCGGC------CCGGCC
85B-BCG    -------------------------------.CG..TT......--------
85B-KAN    .C.T......GGTG.A.A.C..C.GT.T..--...T.C.GATTAT....G.
85C-TUB    ---------------------------.A....TT..---------------
85C-BCG    ----------------------------------------------------

100          110          120         130          140
                     *            *            *           *            *
85A-TUB    CGCCACCGGGAGTGAGGGGCAATGAGCGCCGGGGCAATACTGACAGCAAG
85B-BCG    ...A..----------------------------------------.G.A
85B-KAN    ---.A....C.--------------------------------------
85C-TUB    --.A.....C.------.TCTC...T.C....C------------.G.C
85C-BCG    ----------------------------------------------------
```

FIG. 2A

```
               150       160       170       180       190
                *         *         *         *         *
85A-TUB  ATCACAATTGAGCCCGGCACACATGCGTCGACACATGCCCAGACACTGCGGAA
85B-BCG  TCG...T..------A....G..TGAG.C.....------.C...T.------
85B-KAN  ------------------------------------------.C...T.------
85C-TUB  ..TCG..C......GTC.T.GGTGTGTTT....TC.........------
85C-BCG  --------------------------------------------------

200       210       220       230       240
                *         *         *         *         *
85A-TUB  ATGCCACCTTCAGGCCCGTCGGTCCCGAATTGGCCGTGAACGACCG
85B-BCG  ----------------------------------------------
85B-KAN  ------------G.A.A..AC..T.G.T.TG.....G.--------
85C-TUB  ------------------------------A.AG....--------
85C-BCG  ..............................................

250       260       270       280       290
                *         *         *         *         *
85A-TUB  CCGGATAAGGGTTTCGGCGGTGCGCTTGATGCGGGTGGACGCCCGA----A
85B-BCG  ---..G...CC.A.ATC.AAA...GAA.GAC.T..C..------T
85B-KAN  --------------------------------------------.....TCG.
85C-TUB  --------------------.TC.......A.....A.------
85C-BCG  .
```

FIG. 2A (CONT.)

```
                         300             310              320         * PstI  330
                          *               *                *          ┌──────┐↑
85A-TUB   GTTGTGGTTGACT-ACACG---AGCACTGCCGG---GGGCCCAGCGC│CTGCAG│C
85B-BCG   ...C.........  ......  .............C........  ........   └──────┘A
85B-KAN   CA.T..CCCT...C.....GTA..TT........  ............          ──────
85C-TUB   ──────────────────────────────────  ────────────          ──────A
85C-BCG   ....G.A......  .........TAGT....    ............          ──────

340             350              360          370              380
                          *               *                *           *                *       ↑
85A-TUB   TGACCTAATTCAGGATGCGCCCAAACATGCATGCATGGATGCCGTTGAG│ATGAG-
85B-BCG   C....GAC..A....  ..........GGG...CA.G..   ──────  ──────  ──CA
85B-KAN   ──────────────  ────────C.C...AG..C.T.C.G──────  .AAG.G.CA.G.
85C-TUB   ──────────────  ────────────────────────  ──────  ──────  ──A
85C-BCG   ....G.TC......  ──────────────────────── ──────  ──────  ──────

390             400              410          420              430
                          *       ↑       *                *    ↑       *                *
85A-TUB   GATGAGGGAAGCAAGA│ATGCAGCTTGTTGACAGGGTTCGTGGCCGTCA
85B-BCG   ..C.T.A.CC.A...T.CG.....GG...  ──────  ──────────────
85B-KAN   T...CA..C.TG..CGG.A..A..  ──────  ──────  .C.GG.....G.......A.CG.
85C-TUB   ──────────────  ────────────────────────  .C.GG.....G........A.CG.
85C-BCG   C.G.T.C.......  ────────────────────────  ..T.G...GA....A.CG.
```

FIG. 2A (CONT.)

FIG. 2A (CONT.)

```
                440         450         460         470         480
                 *           *           *           *           *
85A-TUB  CGGGTATGTCGCGTCGACTCGTCGGTGGCCCGTCGGTGGCGGCCCTAGTG
85B-BCG  ----------..C....T.GA..A....CA.G.CA.CG..T.TAG.CC.T
85B-KAN  ----------..C....T.GA..A....CA.G.CA.CG..T.TAG.CC.T
85C-TUB  ----------A..C.TT..G..C.G....CT.CT.......---...T
85C-BCG  .AACCC..C......C...CG.G.CTA....C...TA.G..G..T...G...T 490         500         510         520         530
                 *        *Kpn I         *           *           *
85A-TUB  TCGGGTCTGGTCGGCCGTCGGTGGCCGACCGGCTGGGCA TTTTC
85B-BCG  C..C.....G..GCTT.C...C..AG....C....C...G...C
85B-KAN  C.T..C..........ACT..C....C..AG....C....A...C
85C-TUB  .AC..........TA..T......C..GC.....C.........C
85C-BCG 540         550         560         570         580
                 *           *           *    PstI    *           *
85A-TUB  CCGGCCGGGCTTGCCGGTGGAGTAC CTGCAG GTGCCGTCGCCGTCGATGG
85B-BCG  .........GC...C..................C................
85B-KAN  ...T...C..C......................C................
85C-TUB  ......C...TC.T.A.....A..T...........A..CG.........
85C-BCG  TA.....C...TC.T.A.....A..T...........A..CG.........
```

```
                   740        750        760        770        780
                    *          *          *          *          *
85A-TUB   TCATGCCGGTGGGTGGCCAGTC|AAGCTT|CTACTCCGACTGGTACCAGCCC
85B-BCG   ..........C...C..G....              AG..........AGC..G
85B-KAN   ..........C...C..A....              C...........AGC..G
85C-TUB   ..........C.......C...              C..T.AGT.........
85C-BCG   ............C..C..A...              C..T.A...T.......
          (Hind III boxed at position 757-762)

790        800        810        820        830
                    *          *          *          *          *
                                                              →P79
85A-TUB   GCCTGCGGGCAAGGCCCGGTTGCCAGACTTACAAGTGGGAGACCTTCCTGAC
85B-BCG   ..........................................A.C......
85B-KAN   .............T..C.....C..AC..............C.........
85C-TUB   |T.GCAGA....C.G.CAGAA..T.C|.....................T...
85C-BCG   |T.GCAGA....C.G.CAGAA..T.C|.........................

840        850        860        870        880
                    *          *          *          *          *
85A-TUB   CAGCGAGCTGCCGGGCTGGCTGCAGGCCAACAGGCACGTCAAGCCCACCG
85B-BCG   .........................CAA...T..TCC....GC..G...
85B-KAN   .........................CAA......TCC..G..C..AGT.
85C-TUB   ...A.........A....C.CC......A.........A.GG..GTCC..G..A.
85C-BCG   ...A.........A....C.CC......A..........A.GG..GTCC..G..A.
```

FIG. 2A (CONT.)

```
              890         900         910         920         930
               *           *           *           *           *
85A-TUB  GAAGCGCCGTCGTGTCGGTCGGTGGCTGTCTTTCGATGGCTGTCTTCGGCTGACGCTG
85B-BCG  ....C......T.CAA....CT.G..........C.GC..G......AA...TCT...
85B-KAN  ...........CG......CA.C..........C.GC.TG...C....TC....
85C-TUB  ..C.A...G.CG..G..................T.G.GCGG...C......TC....
85C-BCG 940         950         960         970         980
               *           *           *           *           *
85A-TUB  GCGATCTATCACCCCCAGCAGTTCGTCTACGCGGGAGCGATGTCGGGCCT
85B-BCG  ..CGC....C...............A.........C..CT...C......C....
85B-KAN  T..CG....C.....G.........A...........TT..T......C....
85C-TUB  ..CGCG..CT.....G................CCG......C..CGT..T......T.
85C-BCG 990         1000        1010        1020        1030
               *           *           *           *           *
85A-TUB  GTTGGACCCCTCCCAGGCGATGGGTCCCACCCTGATCGGCCTGGGCGATGG
85B-BCG  ..C........T......G.....G......C..........
85B-KAN  .A...........G.....G..GT.T......T.........
85C-TUB  CC.CA......G...GCTG.T.G..G................A
85C-BCG
```

FIG. 2A (CONT.)

```
           1040      1050      1060      1070      1080
              *         *         *         *         *
85A-TUB  GTGACGCTGGCGGCTACAAGGCCTCCGACATGTGGGCCCGAAGGAGGAC
85B-BCG  .......C.....T.........G.A...........T..CTC.AGT...
85B-KAN  .......C..T..T...........G...........A..CTC.AGT...
85C-TUB  AC...T.G.....T.....C...AA.AG.........T...TCCAGC...
85C-BCG 1090      1100      1110      1120      1130
              *         *         *         *         *
85A-TUB  CCGGCGTGGCAGCGCAACGACCCGCTGTTGAACGTCGGGAAGCTGATCGC
85B-BCG  .....A...G.............TAC.CA.C.GA..CCC......G....
85B-KAN  ..A..C.........T........TC.C..C..A.TCC.G.....G....
85C-TUB  .....C...A.............AA..G.TC.GA.TCCCCGC...G....
85C-BCG 1140      1150      1160      1170      1180
              *         *         *         *         *
85A-TUB  CAACAACACCCGCGTCTGGGTGTACTGCGGCAACGGCAAGCCGTCGGATC
85B-BCG  A...........GC.A.....T..T.....G.......CC...AAC..GT
85B-KAN  .............C.G...A.C.................CC.....C..GT
85C-TUB  ............GA................T.......CA..CAGC..C.
85C-BCG
```

FIG. 2A (CONT.)

```
            1190      1200      1210      1220      1230
               *         *         *         *         *
85A-TUB  TGGGTGGCAACAACCTGCCGGCCAAGTTCCTCGAGGGCTTCGTGCGGACC
85B-BCG  ....C..TGC....A.A..C...G.....T.G...AA......T..T.G.
85B-KAN  ....C..TGC...TG.T......G.A.....G...AA......T..C.G.
85C-TUB  .C..C...G.....A.A.....G........G..A...C..ACC.T.CG.
85C-BCG 1240      1250      1260      1270          1280
               *         *         *         *             *
85A-TUB  AGCAACATCAAGTTCCAAGACGCCTACAACGCCGGTGGCGG----CCACA
85B-BCG  ......C.G........G..T..G.....GC...CG.....----G....
85B-KAN  ......C.G..A.....G................CG.....GCGG.....
85C-TUB  .C....CAG.CC....GG...A.....GCG....AC..T..----A.G..
85C-BCG 1290      1300      1310      1320      1330
                   *         *         *         *         *
85A-TUB  ACGGCGTGTTCGACTTCCCGGACAGCGGTACGCACAGCTGGGAGTACTGG
85B-BCG  ...C.......A........CC..A...C.....................
85B-KAN  ...C.......A.T..GGAC.C..A...A.....................
85C-TUB  ....G.....TA........CC..A...A..A...TCG...CCC......
85C-BCG
```

FIG. 2A (CONT.)

```
                    1340       1350       1360       1370
                     *          *          *          *
85A-TUB    GGGCGCGCAGCTCAACGCTATGAAGCCCGACCTGCAACGGGCA---CTG---
85B-BCG    .........T...........C.........GGT..........GA.TT.G---T.A---
85B-KAN    .........T...........C.........GGT..........GA.TT.G---T.A---
85C-TUB    AA...A........GGT....C.........G.........-.-..C..GC....---
85C-BCG    AA...A........GGT..............G.....TA.C..G.AT.TG--...CAAC 1380       1390       1400       1410
            *          *          *          *
85A-TUB    GGTGCCA---STOP---CGCCCAACACCGGGCCCGCCCCCAGGGC----GCC
85B-BCG    ...C......-------.........................CT---...A.
85B-KAN    ...C...CGCTGAT...G..--...TTGC....TA.T....TTGAC.G.
85C-TUB    ...C...-------...A...CCGG...CC..T..TG.G.C..C...---
85C-BCG                                                   ---

1420   1430       1440       1450       1460
                   *           *          *          *
85A-TUB    STOP---TAG--CTCCGAACAGACACAACA---TCTAGCNNCGGTGACCCTTGTGGNN
85B-BCG    GG.-A.......C.....----.--GG.T......T....----.--.TC
85B-KAN    A..A.G...TCA..C..GT.GTGTG.TCG..AC.TTGA..G..G...CCGC
85C-TUB    ---------------------G.---G.....G.C.....---
85C-BCG    .:---
```

FIG. 2A (CONT.)

```
                -40             -30             -20             -10              +1         +10
                 *               *               *               *               *           *
85A      MQL---VDRVRGAVTGMSRRLVVGAVGAALVSGLVGAVGGTATAGAFSRPGLPVEYLQVP
85B      .TD---.S.KIR.---WG...MI.TAA.VVLP....LA....LA......A........
85B-Ka   ------TD.S.KIRAWG...L..AA..ALP.....LA....LA......A........
85C      .TFFEQ.R.L.S.A.TLP..VAIA.M..V..Y...TF....P.......P........

20              30              40              50              60          70
                 *               *               *               *               *           *
85A      SPSMGRDIKVQFQSGGANSPALYLLDGLRAQDDFSGWDINTPAFEWYDQSGLSVVMPVGG
85B      ...........................N..V.........YN..........Y....I...
85B-Ka   .AA..S.....................D..V.........YN..........Y....I...
85C      .A.........................--PH.V.......YN........E.Y....I...
85C-BCG  ...........................--PH.V.......YN........E.Y....I...

80              90             100             110             120         130
                 *               *               *               *               *           *
85A      QSSFYSDWYQPACGKAGCQTYKWETFLTSELPGWLQANRHVKPTGSAVVGLSMAASSALT
85B      .......S.......T......L......Q.S..A......AI....G....MI
85B-Ka   .....T......SQSNGQNY...........Q.S..S.....A..I....G.....I
85C      .....T......SQSNGQNY.........R.M.A....KG.S...N.A....SGG...I
85C-BCG  ..............................R.M.A....KG.S...N.A....SGG...I
```

FIG. 2B

```
            140       150       160       170       180       190
             *         *         *         *         *         *
85A     LAIYHPQQFVYAGAMSCLLDPSQAMGPTLIGLAMGDAGGYKASDMWGPKEDPAWQRNDPL
85B     ..A.....I.....SL.A......G...S..........A....SS....E....T
85B-Ka  .SV.....I.....SL.A.M....G...S..........................S
85C     ..A.Y...P..ASL.F.N.EGWW..........N.S....N.NS....SS....K....M 200       210       220       230       240       250
             *         *         *         *         *         *
85A     LNVGKLIANNTRVWVYCGNGKPSDLGGNNLPAKFLEGFVRTSNIKFQDAYNAGGIINGVF
85B     QQIP..V......L......T.NE...A.I.E...N...S..L....KPA.....A..
85B-Ka  .HIPE.V......L.I.....T.E...A.V..E...N...S..L.........A..
85C     VQIPR.V......I.......T........D.I......LTLRT.QT.R.T.A.D..R....

260       270       280       290
             *         *         *         *
85A     DFPDSGTHSWEYWGAQLNAMKPDLQRAL-GATPNTGPAPQGA
85B     N..PN..................G...SS..-..-------G
85B-Ka  NLDAN..................G...AS..-..-------R
85C     N..PN.......P..NE..V...A.I.HV.N...PAA..APA.
```

FIG. 2B (CONT.)

NUCLEIC ACIDS, VECTORS, AND HOST CELLS INCLUDING MYCOBACTERIUM DERIVED SEQUENCES

BACKGROUND OF THE INVENTION

1. Field of the Invention

The invention relates to polypeptides and peptides, particularly recombinant polypeptides and peptides, which can be used for the diagnosis of tuberculosis. The invention also relates to a process for preparing the above-said polypeptides and peptides, which are in a state of biological purity such that they can be used as part of the active principle in the preparation of vaccines against tuberculosis.

It also relates to nucleic acids coding for said polypeptides and peptides.

Furthermore, the invention relates to the in vitro diagnostic methods and kits using the above-said polypeptides and peptides and to the vaccines containing the above-said polypeptides and peptides as active principle against tuberculosis.

By "recombinant polypeptides or peptides" it is to be understood that it relates to any molecule having a polypeptidic chain liable to be produced by genetic engineering, through transcription and translation, of a corresponding DNA sequence under the control of appropriate regulation elements within an efficient cellular host. Consequently, the expression "recombinant polypeptides" such as is used herein does not exclude the possibility for the polypeptides to comprise other groups, such as glycosylated groups.

The term "recombinant" indeed involves the fact that the polypeptide has been produced by genetic engineering, particularly because it results from the expression in a cellular host of the corresponding nucleic acid sequences which have previously been introduced into the expression vector used in said host.

Nevertheless, it must be understood that this expression does not exclude the possibility for the polypeptide to be produced by a different process, for instance by classical chemical synthesis according to methods used in the protein synthesis or by proteolytic cleavage of larger molecules.

The expression "biologically pure" or "biological purity" means on the one hand a grade of purity such that the recombinant polypeptide can be used for the production of vaccinating compositions and on the other hand the absence of contaminants, more particularly of natural contaminants.

2. Description of the Prior Art

Tuberculosis remains a major disease in developing countries. The situation is dramatic in some countries, particularly where high incidence of tuberculosis among AIDS patients represents a new source of dissemination of the disease.

Tuberculosis is a chronic infectious disease in which cell-mediated immune mechanisms play an essential role both for protection against and control of the disease.

Despite BCG vaccination, and some effective drugs, tuberculosis remains a major global problem. Skin testing with tuberculin PPD (protein-purified derivative) largely used for screening of the disease is poorly specific, due to cross reactivity with other pathogenic or environmental saprophytic mycobacteria.

Moreover, tuberculin PPD when used in serological tests (ELISA) does not permit discrimination between patients who have been vaccinated by BCG, or those who have been primo-infected, from those who are developing evolutive tuberculosis and for whom an early and rapid diagnosis would be necessary.

A protein with a molecular weight of 32-kDa has already been purified from zinc deficient *M. bovis BCG* culture filtrate. This protein was identified as antigen 85A (De Bruyn J. et al., 1987, "Purification, partial characterization and identification of a 32-kDa protein antigen of *Mycobacterium bovis BCG*" Microb. Pathogen. 2:351). Its $NH_2$-terminal amino acid sequence (Phe-Ser-Arg-Pro-Gly-Leu) (SEQ ID NO:1) is identical to that reported for the α-antigen (antigen 85B) protein purified from *M. bovis BCG* (Wiker, H. G. et al., 1986, "MPB59, a widely cross-reacting protein of *Mycobacterium bovis BCG*" Int. Arch. Allergy Appl. Immunol. 81:307). The antigen 85-complex is present among different strains of mycobacteria (De Bruyn J. et al., 1989, "Effect of zinc deficiency of the appearance of two immunodominant protein antigens (32-kDa and 65-kDa) in culture filtrates of Mycobacteria" J. Gen Microbiol. 135:79). It is secreted by living bacilli as a predominant protein in normal Sauton culture filtrate and could be useful in the serodiagnosis of tuberculosis (Turneer M. et al., 1988, "Humoral immune response in human tuberculosis: immunoglobulins G, A and M directed against the purified P32 protein antigen of *Mycobacterium bovis bacillus Calmette-Guerin*" J. Clin. Microbiol. 26:1714) and leprosy (Rumschlag H. S. et al., 1988, "Serological response of patients with lepromatous and tuberculosis leprosy to 30-, 31- and 32-kilodalton antigens of *Mycobacterium tuberculosis*" J. Clin. Microbiol. 26:2200). Furthermore, the 32-kDa protein-induced specific lymphoproliferation and interferon-γ(IFN-γ) production in peripheral blood leucocytes from tuberculosis (Huygen K. et al., 1988, "Specific lymphoproliferation, γ-interferon production and serum immunoglobulin G directed against a purified 32-kDa mycobacterial antigen (P32) in patients with active tuberculosis" Scand. J. Immunol. 27:187), and leprosy patients and from PPD- and lepromin-positive healthy subjects. Recent findings indicate that the amount of 32 kDa protein induced IFN-γ in BCG-sensitized mouse spleen cells is under probable H-2 control (Huygen K. et al, 1989, "H-2-linked control of in vitro γ interferon production in response to a 32-kilodalton antigen (P32) of *Mycobacterium bovis bacillus Calmette-Guérin*" Infect. Imm. 56:3196). Finally, the high affinity of mycobacteria for fibronectin is related to proteins of the antigen 85-complex (Abou-Zeid C. et al., 1988, "Characterization of fibronectin-binding antigens released by *Mycobacterium tuberculosis* and *Mycobacterium bovis BCG*" Infect. Imm. 56:3046).

Wiker et al. (Wiker H. G. et al., 1990, "Evidence for three separate genes encoding the proteins of the mycobacterial antigen 85 complex" Infect. Immun. 58:272) showed recently that the antigens 85A, B and C isolated from *M. bovis BCG* culture filtrate present a few amino acid replacements in their $NH_2$ terminal region strongly suggesting the existence of multiple genes coding for these proteins. But, the data given for the antigen 85C of *M. bovis BCG* are insufficient to enable its unambiguous identification as well as the characterization of its structural and functional elements.

The gene encoding the 85A antigen from *Mycobacterium tuberculosis* has been described (Borremans L. et al., 1989, "Cloning, sequence determination and expression of a 32-kilodalton protein gene of *Mycobacterium tuberculosis*" Infect. Immun. 57:3123) which presented 77.5% homology at the DNA level within the coding region with the α-antigen gene (85B gene of *M. bovis BCG*, substrain Tokyo) (Matsuo K. et al., 1988, "Cloning and expression of the *Mycobacte-*

*rium bovis BCG* gene for extracellular α-antigen" J. Bacteriol. 170:3847). Moreover, recently a corresponding 32-kDa protein genomic clone from a λgt11 BCG library (prepared from strain *M. bovis BCG* 1173P2) was isolated and sequenced. The complete sequence of this gene is identical with that from the 85A gene of *Mycobacterium tuberculosis* except for a single silent nucleotide change (De Wit L. et al., 1990, "Nucleotide sequence of the 32 kda-protein gene (antigen 85A) of *Mycobacterium bovis BCG*" Nucl. Ac. Res. 18:3995). Thus, it was likely, but not demonstrated, that the genome of *M. bovis BCG* contained at least two genes coding for antigen 85A and 85B respectively. As to the genome of the *Mycobacterium tuberculosis* and *M. bovis*, nothing was proved as to the existence of new genes, besides the genes coding respectively for 85A and 85B.

SUMMARY OF THE INVENTION

An aspect of the invention is to provide a new family of nucleic acids coding for new proteins and polypeptides which can be used for the detection and control of tuberculosis.

Another aspect of the invention is to provide nucleic acids coding for the peptidic chains of biologically pure recombinant polypeptides which enable their preparation on a large scale.

Another aspect of the invention is to provide antigens which can be used in serological tests as an in vitro rapid diagnostic test for tuberculosis or in skin test, or as immunogenic principle of a vaccine.

Another aspect of the invention is to provide a rapid in vitro diagnostic means for tuberculosis, enabling it to discriminate between patients suffering from an evolutive tuberculosis from those who have been vaccinated against BCG or who have been primo-infected.

Another aspect of the invention is to provide nucleic probes which can be used as in vitro diagnostic reagents for tuberculosis as well as in vitro diagnostic reagents for identifying *M. tuberculosis* from other strains of mycobacteria.

BRIEF DESCRIPTION OF THE DRAWINGS

FIG. 1 represents the nucleotide (SEQ ID NO:2) and amino acid sequence of (SEQ ID NO:3) the 85C antigen containing region of *M. tuberculosis.*

The previously identified 28-residue $NH_2$ terminal amino acid sequence of the mature protein is underlined with a double line. One additional ATG codon, downstream from the ATG at position 150 is underlined. Since the precise length of the signal sequence could not be determined, the option taken here represents the 46 amino acid signal peptide corresponding to $ATG_{150}$. The putative signal peptide is represented in italic capitals. The top drawing represents the sequencing strategy. Arrows indicate the direction of dideoxy-sequencing either in DNA subcloned as double-stranded DNA in Blue Scribe M13+ or as single stranded DNA in the mp18 M13 vector. The entire sequence was determined using synthetic oligonucleotides represented as gray boxes in the figure.

FIG. 2 represents the homology between known nucleotide and amino acid sequence of the antigen 85 and the 85C antigen of *M. tuberculosis.*

A-Comparison of the DNA sequences of antigen 85A, B, and C:

DNA sequences have been aligned with the "Align" program which visualizes multiple alignments. In this presentation, sequence differences are outlined:

(•) indicate identical residues; (–) indicates a gap; (any letter) indicates a substitution.

All sequences are compared and aligned to the first line (gene 85A).

85A-TUB: DNA sequence from *M. tuberculosis* (Borremans L. et al., 1989, "Cloning, sequence determination and expression of a 32-kilodalton protein gene of *Mycobacterium tuberculosis", Infect. Immun.* 57:3123).

85B-BCG: DNA sequence from α-antigen of *Mycobacterium bovis* (strain Tokyo) (Matsuo K. et al., 1988, "Cloning and expression of the *Mycobacterium bovis BCG* gene for extracellular α-antigen", *J. Bacteriol.* 170:3847).

85C-TUB: DNA sequence from antigen 85C from *Mycobacterium tuberculosis* (the present invention).

85B-KAN: DNA sequence from antigen 85B from *M. kansasii* (Matsuo K. et al., 1990, "Cloning and expression of the gene for cross-reactive α antigen of *Mycobacterium kansasii", Infect. Immun.* 58:550).

85C-BCG: Partial DNA sequence from *Mycobacterium bovis BCG* strain 1173P2 (the present invention). This sequence was obtained from a cloned PCR amplified DNA fragment.

↱ indicates the presumed initiation codon for each gene.

(↓) indicates the first phenylalanine residue of the mature protein.

STOP indicates the termination codon of each gene.

P78 and P79 are sense and antisense primers used for PCR amplification.

85A, -B, -C sequences used for the synthesis of specific synthetic oligonucleotide probes are framed.

The indicated restriction sites have been used to prepare the three type-specific probes (see also FIG. 4A).

B- Comparison of the pre-protein sequences of antigen 85A, B and C:

DNA sequences have been aligned with the "Align" program which visualizes multiple alignments. In this presentation, sequence differences are outlined:

(•) indicate identical residues; (–) indicates a gap; (any letter) indicates a substitution.

All sequences are compared and aligned to the first line (gene 85A).

85A: Protein sequence from *M. tuberculosis* (Borremans L. et al., 1989, "Cloning, sequence determination and expression of a 32-kilodalton protein gene of *Mycobacterium tuberculosis", Infect. Immun.* 57:3123).

85B: Protein sequence from α-antigen of *Mycobacterium bovis* (strain Tokyo) (Matsuo K. et al., 1988, "Cloning and expression of the *Mycobacterium bovis BCG* gene for extracellular α-antigen", *J. Bacteriol.* 170:3847).

85C: Protein Sequence from antigen 85C from *Mycobacterium tuberculosis* (the present invention).

85B-KAN: Partial protein sequence from antigen 85B from *M. kansasii* (Matsuo K. et al., 1990, "Cloning and expression of the gene for cross-reactive α antigen of *Mycobacterium kansasii", Infect. Immun.* 58:550).

85C-BCG: Partial protein sequence from *Mycobacterium bovis BCG* strain 1173P2 (the present invention).

The "C" characteristic motif is framed.

FIG. 3 represents the hydropathy pattern of the *M. tuberculosis* 32-kDa (antigen 85A), the α-antigen of BCG (antigen 85B) and antigen 85C from *M. tuberculosis*, amino acid sequences:

The sequence of the three pre-proteins (including the presumed signal peptide signals) have been analyzed using the Kyte and Doolittle method (Borremans L. et al., 1989, "Cloning, sequence determination and expression of a 32-kilodalton protein gene of *Mycobacterium tuberculosis*", *Infect. Immun.* 57:3123) with a window of eight amino acids. Each bar on the axes represents 50 amino acids. Since the length of signal sequences are slightly different (43, 40 and 46 residues for the three proteins 85A, 85B, 85C) the patterns are aligned to the first residue of the three mature proteins. Plain lines are used to align hydrophobic peaks and a dashed line to align hydrophilic peaks.

Figure 4A:
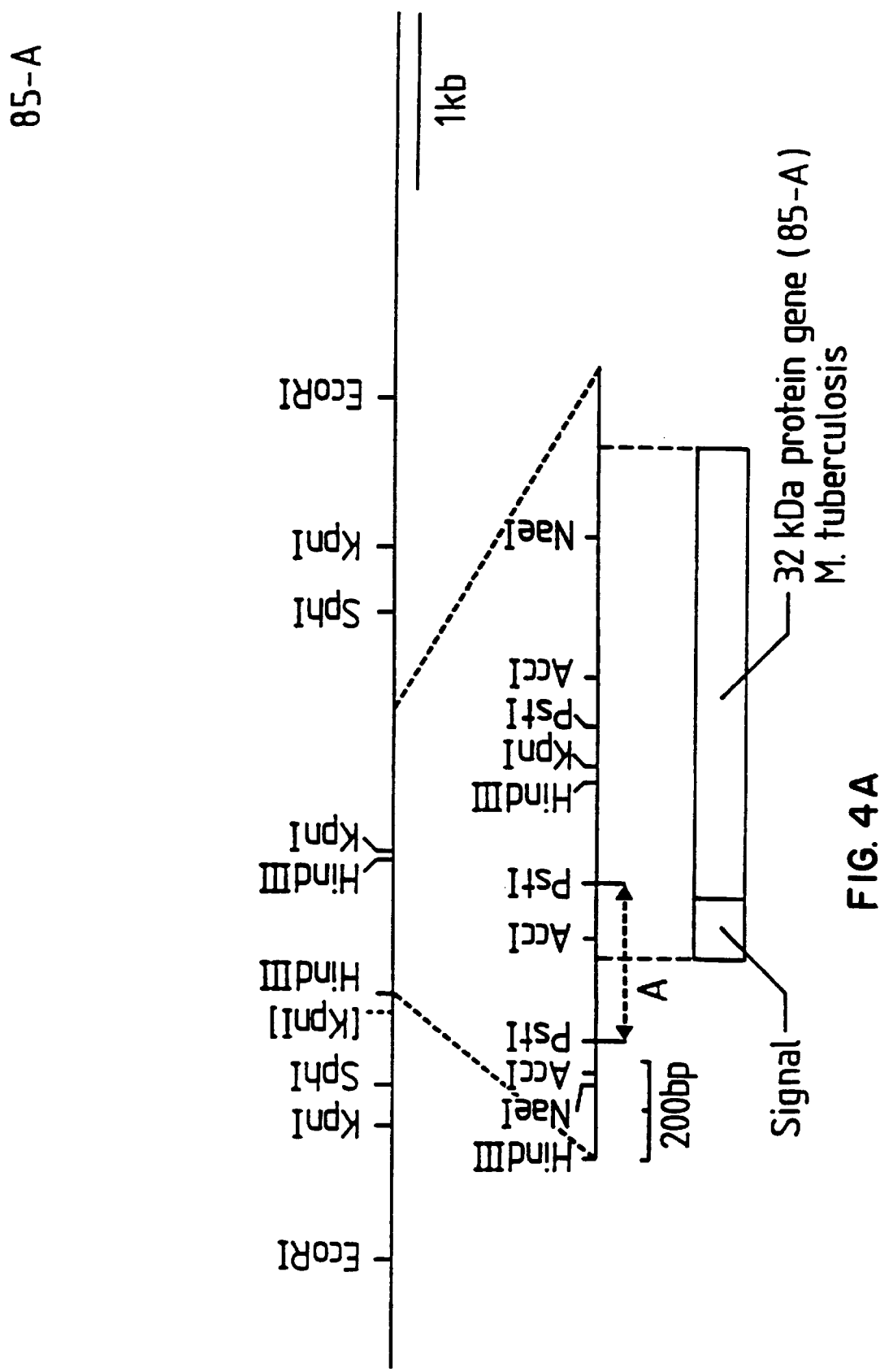
Figure 4A:
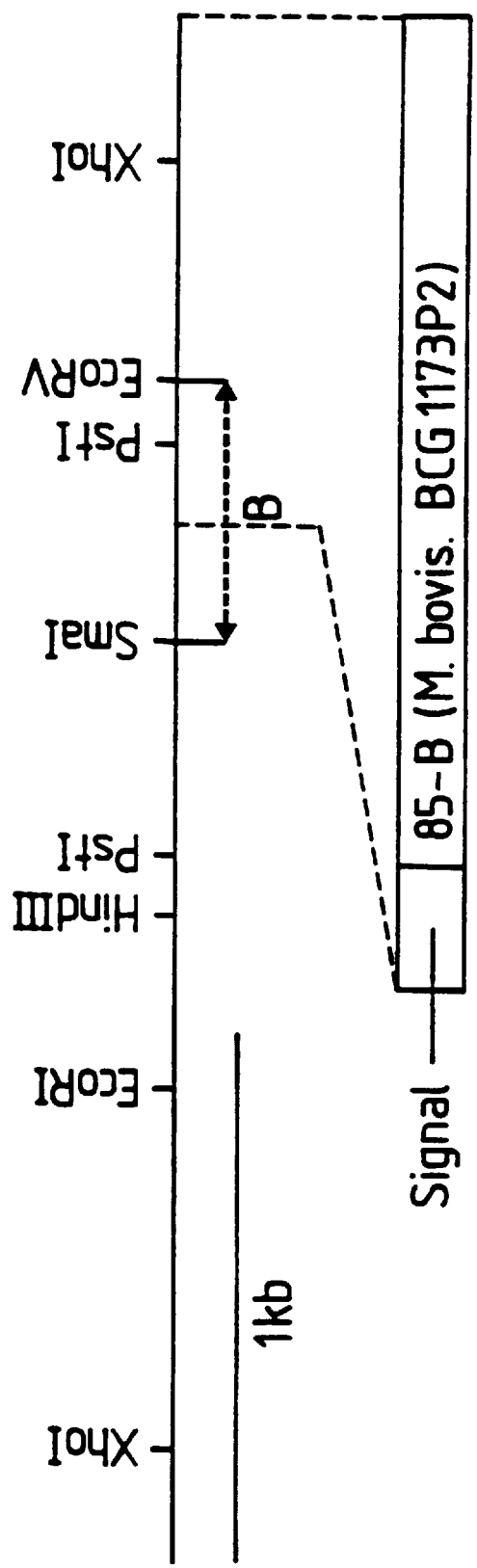
Figure 4A:
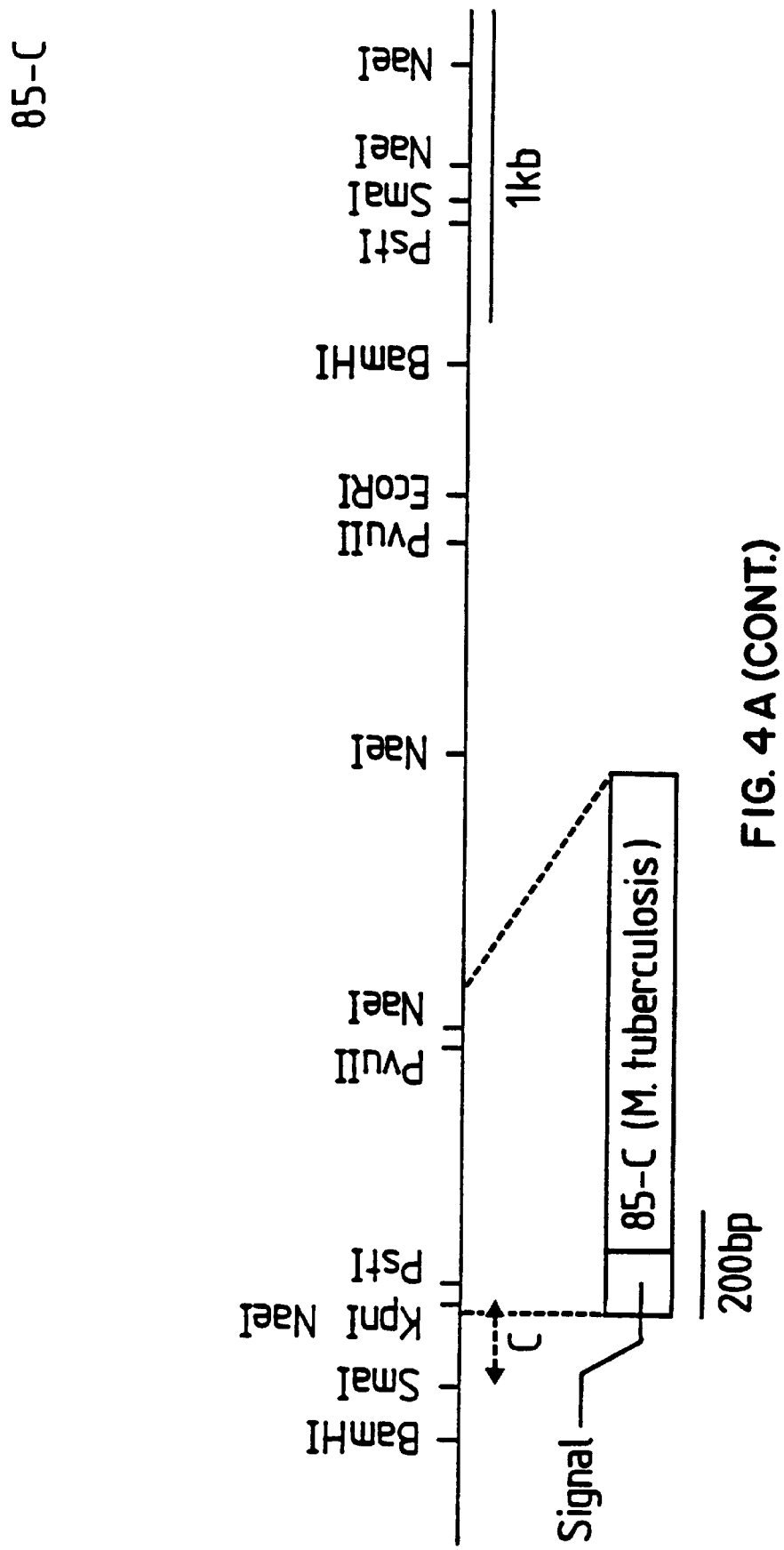

FIGS. 4A represents the restriction endonuclease maps of the three genes 85A, 85B and 85C: type-specific probes are marked by <-->.

The map of gene 85A is derived from Borr et al. (Borremans L. et al., 1989, "Cloning, sequence determination and expression of a 32-kilodalton protein gene of *Mycobacterium tuberculosis*", *Infect. Immun.* 57:3123). The map of 85B was obtained from clone 5.1 derived for our *Mycobacterium bovis BCG* 1173P2 λgt11 recombinant library (De Wit L. et al., 1990, "Nucleotide sequence of the 32 kDa-protein gene (antigen 85A) of *Mycobacterium bovis BCG*", *Nuc. Ac. Res.* 18:3995). For the restriction enzymes used, this map is identical to that published for *M. bovis BCG* (strain Tokyo) (Matsuo K. et al., 1988, "Cloning and expression of the *Mycobacterium bovis BCG* gene for extracellular α antigen", *J. Bacteriol.* 170:3847). The coding region of the 85B antigen is positioned according to Matsuo et al. (Matsuo et al., 1988, "Cloning and expression of the *Mycobacterium bovis BCG* gene for extracellular α-antigen", *J. Bacteriol.* 170:3847).

The map of 85C corresponds to the restriction map of clone 11.2 that was obtained from the *M. tuberculosis* λgt11 library from R. Young (Young, R. A. et al., 1985, "Dissection of *Mycobacterium tuberculosis* antigens using recombinant DNA", *Proc. Natl. Acad. Sci. USA* 82:2583) (Materials and Methods). The position of the specific 5' DNA restriction fragment used for Southern analysis is indicated in each map by a double arrow.

Figure 4B:
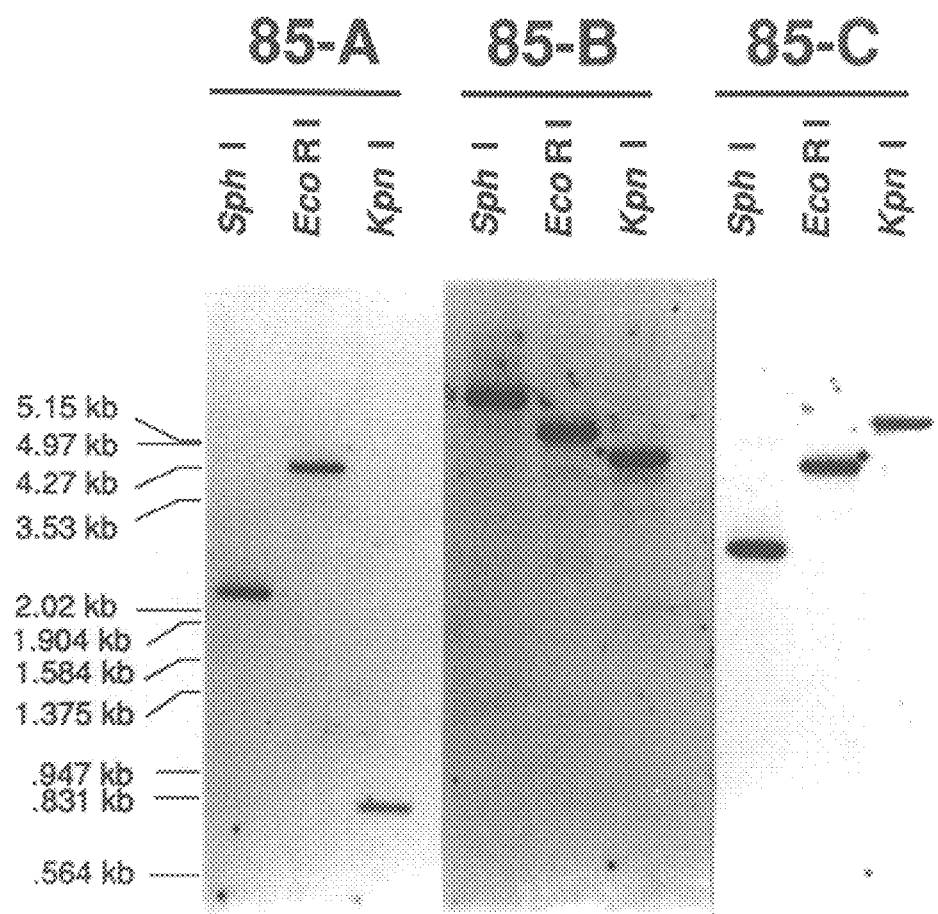

FIG. 4B represents the Southern analysis of the total genomic DNA from *Mycobacterium bovis BCG* (strain 1173P2).

Fifteen μg of digested DNA was applied per lane. Hybridization was with oligonucleotide probes A, B, C (as described in FIG. 2A) under the conditions described in Materials and Methods. Molecular weight of the hybridizing bands were calculated by comparison with standards.

Figure 4C:
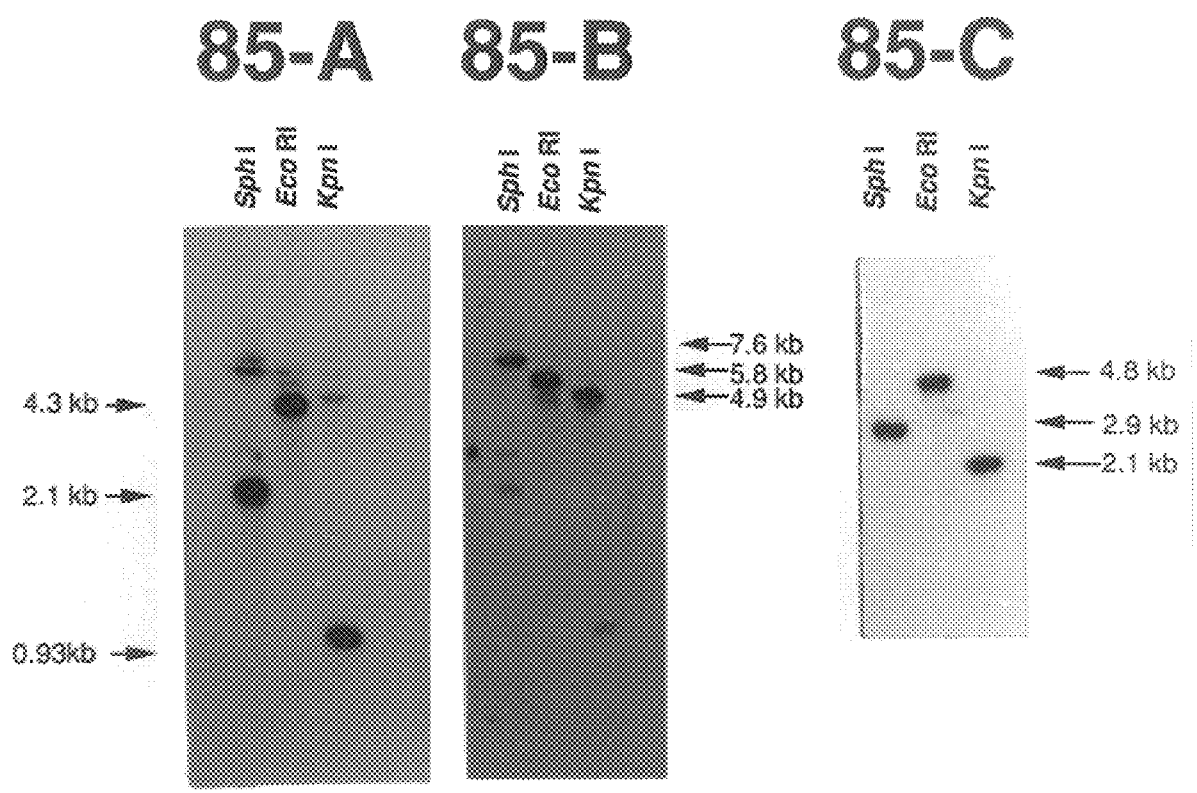

FIG. 4C represents the Southern analysis of total genomic DNA from *M. bovis BCG* 1173P2. The procedure described for FIG. 4B was used.

The three probes, however, were large DNA restriction fragments (as defined in FIG. 4A).

Parts 85A and 85B were obtained from a single filter, whereas 85C was from a separate run.

Figure 5:
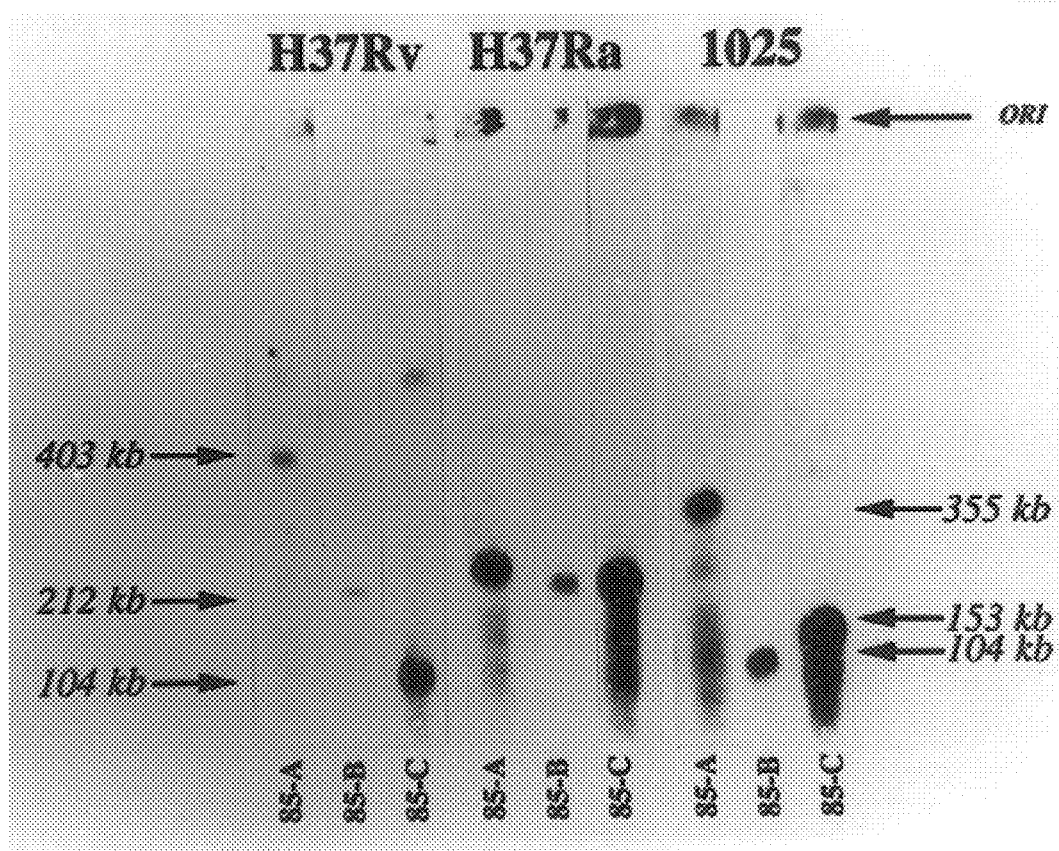

FIG. 5 represents the pulse field electrophoresis of *Mycobacterium tuberculosis* DNA.

DNA from three strains of *Mycobacterium tuberculosis* was digested with DraI and separated by Pulso field electrophoresis on an agarose gel together with a bacteriophage λ DNA "ladder" as described in Materials and Methods. After transfer to nylon filters, hybridization with the three probes 85A, 85B, 85C was as described under FIG. 4A. Molecular weights of the hybridizing bands were calculated by comparison with those of the λ DNA "ladder".

The nucleic acids of the invention
contain a nucleotide sequence extending from the extremity constituted by the nucleotide at position (1) to the extremity constituted by the nucleotide at position (149) represented on FIG. 1 (SEQ ID NO:2),
or contain one at least of the nucleotide sequences coding for the following peptides or polypeptides:
the one extending from the extremity constituted by amino acid at position (−46) to the extremity constituted by amino acid at position (−1) represented on FIG. 1 (SEQ ID NO:3), or
the one extending from the extremity constituted by amino acid at position (−21) to the extremity constituted by amino acid at position (−1) represented on FIG. 1 (SEQ ID NO:3), or
SQSNGQNY (SEQ ID NO:4), or
PMVQIPRLVA (SEQ ID NO:5), or
GLTLRTNQTFRDTYAADGGRNG (SEQ ID NO:6), or
PPAAPAAPAA (SEQ ID NO:7),
or contain nucleotidic sequences:
hybridizing with the above-mentioned nucleotide sequences, or their complements,
complementary to the above-mentioned nucleotide sequences, or
which are the above-mentioned nucleotide sequences wherein T can be replaced by U,
or are constituted by the above-mentioned nucleotide sequences.

SQSNGQNY (SEQ ID NO:4) is a sequence corresponding to the one extending from position 84 to position 91 of 85C sequence represented on FIG. 1.

PMVQIPRLVA (SEQ ID NO:5) is a sequence corresponding to the one extending from position 191 to position 200 of 85C sequence represented on FIG. 1.

GLTLRTNQTFRDTYAADGGRNG (SEQ ID NO:7) is a sequence corresponding to the one extending from position 229 to position 250 of 85C sequence represented on FIG. 1.

PPAAPAAPAA (SEQ ID NO:7) is a sequence corresponding to the one extending from position 285 to position 294 of 85C sequence represented on FIG. 1.

The hybridization takes place under the following conditions:
hybridization and wash medium:
a preferred hybridization medium contains about 3×SSC [SSC=0.15M sodium chloride, 0.015M sodium citrate, pH 7] about 25 mM of phosphate buffer pH 7.1, and 20% deionized formamide, 0.02% Ficoll, 0.02% BSA, 0.02% polyvinylpyrrolidone and about 0.1 mg/ml sheared denatured salmon sperm DNA,
a preferred wash medium contains about 3×SSC, about 25 mM phosphate buffer, pH 7.1 and 20% deionized formamide;
hybridization temperature (HT) and wash temperature (WT) are between 45° C. and 65° C.;
for the nucleotide sequence extending from the extremity constituted by the nucleotide at position (1) to the extremity constituted by the nucleotide at position (149) represented on FIG. 1: HT=WT=65° C. for the nucleic acids of the invention defined by coded polypeptides X–Y: i.e.
the sequence extending from the extremity constituted by the amino acid at position (X) to the extremity constituted by the amino acid at position (Y) represented on FIG. 1, the sequence extending from the extremity constituted by the amino acid at position (−46) to the extremity constituted by the amino acid at position (−1) represented on FIG. 1, HT=WT=65° C.

the sequence extending from the extremity constituted by the amino acid at position (−21) to the extremity constituted by the amino acid at position (−1) represented on FIG. 1, HT=WT=60° C. for the nucleic acids defined by coded polypeptides represented by their sequence:

SQSNGQNY (SEQ ID NO:4) HT=WT=45° C.

PNVQIPRLVA (SEQ ID NO:5) HT=WT=55° C.

GLTLRTNQTFRDTYAADGGRNG (SEQ ID NO:6) HT=WT=65° C.

PPAAPAAPAA (SEQ ID NO:7) HT=WT=65° C.

The above-mentioned temperatures are to be expressed as approximately ±5° C.

Advantageous nucleic acids of the invention contain at least one of the following nucleotide sequences:

the one extending from the extremity constituted by the nucleotide at position (150) to the extremity constituted by the nucleotide at position (287) on FIG. 1, the one extending from the extremity constituted by the nucleotide at position (224) to the extremity constituted by the nucleotide at position (287) on FIG. 1, the one extending from the extremity constituted by the nucleotide at position (537) to the extremity constituted by the nucleotide at position (560) on FIG. 1, the one extending from the extremity constituted by the nucleotide at position (858) to the extremity constituted by the nucleotide at position (887) on FIG. 1, the one extending from the extremity constituted by the nucleotide at position (972) to the extremity constituted by the nucleotide at position (1037) on FIG. 1, the one extending from the extremity constituted by the nucleotide at position (1140) to the extremity constituted by the nucleotide at position (1169) on FIG. 1, or contain nucleotidic sequences:

hybridizing with the above-mentioned nucleotide sequences, or complementary to the above-mentioned nucleotide sequences, or which are the above-mentioned nucleotide sequences wherein T can be replaced by U, or are constituted by the above-mentioned nucleotide sequences.

The hybridization takes place under the following conditions:

hybridization and wash medium are as defined above;

hybridization temperature (HT) and wash temperature (WT) for the nucleic acids of the invention defined by X–Y: i.e. by the sequence extending from the extremity constituted by the nucleotide at position (X) to the extremity constituted by the nucleotide at position (Y) represented on FIG. 1:

(150)–(287) HT=WT=65° C.

(224)–(287) HT=WT=60° C.

(537)–(560) HT=WT=45° C.

(858)–(887) HT=WT=55° C.

(972)–(1037) HT=WT=65° C.

(1140)–(1169) HT=WT=65° C.

An advantageous group of nucleic acids of the invention contains the nucleotide sequence coding for the following peptide:

SQSNGQNY (SEQ ID NO:4)

and possibly containing the nucleotide sequence coding for the following peptide:

FSRPGLPVEYLQVP (SEQ ID NO:8)

and liable to hybridize with the following nucleotide sequence:

CGGCTGGGAC(or T)ATCAACACCCCGGC (SEQ ID NO:9)

and liable to hybridize neither with

GCCTGCGGCAAGGCCGGTTGCCAG (SEQ ID NO:10)

nor with

GCCTGCGGTAAGGCTGGCTGCCAG (SEQ ID NO:11)

nor with

GCCTGCGGCAAGGCCGGCTGCACG (SEQ ID NO:12)

or are constituted by the above-mentioned hybridizing nucleotide sequences.

The above-mentioned hybridization can take place when the hybridization and wash medium is as indicated above; and the hybridization and wash temperature is 52° C.

The expression "not liable to hybridize with" means that the nucleic acid molecule of the invention does not contain a stretch of nucleotide hybridizing at 52° C. in the above defined medium with the three probes defined above.

Advantageous nucleic acids of the invention contain one at least of the above-mentioned nucleotide sequences or are constituted by the above-mentioned nucleotide sequences and besides contain an open reading frame coding for a polypeptide:

liable to react selectively with human sera from tuberculosis patients and particularly patients developing an evolutive tuberculosis, or liable to be recognized by antibodies also recognizing the amino acid sequence extending from the extremity constituted by amino acid at position (1) to the extremity constituted by amino acid at position (294) represented on FIG. 1, or liable to generate antibodies recognizing the amino acid sequence extending from the extremity constituted by amino acid at position (1) to the extremity constituted by amino acid at position (294) represented on FIG. 1.

The recognition of the above-mentioned sequence of the 294 amino acids (or of the polypeptides of the invention) by the above said antibodies means that the above-said sequence forms a complex with one of the above-mentioned antibodies.

Forming a complex between the antigen (i.e. the sequence of 294 amino acids or any polypeptide of the invention) and the antibodies and detecting the existence of a formed complex can be done according to classical techniques (such as the one using a tracer labeled with radioactive isotopes or an enzyme).

Hereafter is given, in a non-limitative way, a process for testing the selective reaction between the antigen and human sera from tuberculosis patients and particularly patients developing an evolutive tuberculosis.

This test is an immunoblotting (Western blotting) analysis, in the case where the polypeptides of the invention are obtained by recombinant techniques. This test can also be used for polypeptides of the invention obtained by a different preparation process. After sodium dodecyl sulfate—polyacrylamide gel electrophoresis, polypeptides of the invention are blotted onto nitrocellulose membranes (Hybond C. (Amersham)) as described by Towbin H. et al., 1979, "Electrophoretic transfer of proteins from polyacrylamide gels to nitrocellulose sheets: procedure and some applications" Proc. Natl. Acad. Sci. USA 76:4350–4354. The expression of polypeptides of the invention fused to β-galactosidase in *E. coli* Y1089, is visualized by the binding of a polyclonal rabbit anti-antigen 85 serum (1:1, 000) or by using a monoclonal anti-β-galactosidase antibody (Promega). The secondary antibody (alkaline phosphatase anti-rabbit immunoglobulin G and anti-mouse alkaline phosphatase immunoglobulin G conjugates, respectively) is diluted as recommended by the supplier (Promega).

In order to identify selective recognition of polypeptides of the invention and of fusion proteins of the invention by human tuberculous sera, nitrocellulose sheets are incubated overnight with these sera (1:50) (after blocking aspecific protein-binding sites). Reactive areas on the nitrocellulose sheets are revealed by incubation with peroxidase-conjugated goat anti-human immunoglobulin G antibody (Dakopatts, Copenhagen, Denmark) (1:200) for 4 h. After repeated washings, color reaction is developed by adding peroxidase substrate (α-chloronaphtol)(Bio-Rad Laboratories, Richmond, Calif.) in the presence of peroxidase and hydrogen peroxide.

Advantageous nucleic acids of the invention contain or are constituted by one of the above-mentioned nucleotide sequences, contain an open reading frame and code for a mature polypeptide of about 30 to about 35 kD, and contain a sequence coding for a signal sequence.

Advantageous nucleic acids of the invention contain one at least of the nucleotide sequences coding for the following polypeptides:
- the one extending from the extremity constituted by amino acid at position (−46) to the extremity constituted by amino acid at position (−1) represented on FIG. 1, or
- the one extending from the extremity constituted by amino acid at position (−21) to the extremity constituted by amino acid at position (−1) represented on FIG. 1, or
- the one extending from the extremity constituted by amino acid at position (−46) to the extremity constituted by amino acid at position (294) represented on FIG. 1, or
- the one extending from the extremity constituted by amino acid at position (−21) to the extremity constituted by amino acid at position (294) represented on FIG. 1, or
- the one extending from the extremity constituted by amino acid at position (1) to the extremity constituted by amino acid at position (294) represented on FIG. 1, or contain nucleotidic sequences:
  - hybridizing with the above-mentioned nucleotide sequences, or
  - complementary to the above-mentioned nucleotide sequences, or
  - which are the above-mentioned nucleotide sequences wherein T can be replaced by U, or are constituted by the above-mentioned nucleotide sequences.

The hybridization takes place under the following conditions:
- hybridization and wash medium are as above defined;
- hybridization temperature (HT) and wash temperature (WT) for the nucleic acids of the invention defined by coded polypeptides X–Y: i.e. by the coded sequence extending from the extremity constituted by the amino acid at position (X) to the extremity constituted by the amino acid at position (Y) represented on FIG. 1:

(−46)–(−1) HT=WT=65° C.
(−21)–(−1) HT=WT=60° C.
(−46)–(294) HT=WT=70° C.
(−21)–(294) HT=WT=70° C.
(1)–(294) HT=WT=70° C.

Advantageous nucleic acids of the invention contain one at least of the following nucleotide sequences:
- the one extending from the extremity constituted by the nucleotide at position (150) to the extremity constituted by the nucleotide at position (287) represented on FIG. 1, or
- the one extending from the extremity constituted by the nucleotide at position (224) to the extremity constituted by the nucleotide at position (287) represented on FIG. 1, or
- the one extending from the extremity constituted by the nucleotide at position (1) to the extremity constituted by the nucleotide at position (1169) represented on FIG. 1, or
- the one extending from the extremity constituted by the nucleotide at position (150) to the extremity constituted by the nucleotide at position (1169) represented on FIG. 1, or
- the one extending from the extremity constituted by the nucleotide at position (224) to the extremity constituted by the nucleotide at position (1169) represented on FIG. 1, or
- the one extending from the extremity constituted by the nucleotide at position (288) to the extremity constituted by the nucleotide at position (1169) represented on FIG. 1,
- the one extending from the extremity constituted by the nucleotide at position (1) to the extremity constituted by the nucleotide at position (1211) represented on FIG. 1,
- the one extending from the extremity constituted by the nucleotide at position (150) to the extremity constituted by the nucleotide at position (1211) represented on FIG. 1,
- the one extending from the extremity constituted by the nucleotide at position (224) to the extremity constituted by the nucleotide at position (1211) represented on FIG. 1,
- the one extending from the extremity constituted by the nucleotide at position (288) to the extremity constituted by the nucleotide at position (1211) represented on FIG. 1, or contain nucleotidic sequences:
  - hybridizing with the above-mentioned nucleotide sequences, or
  - complementary to the above-mentioned nucleotide sequences, or
  - which are the above-mentioned nucleotide sequences wherein T can be replaced by U, or are constituted by one at least of the following nucleotide sequences.

The hybridization takes place under the following conditions:
- hybridization and wash medium are as above defined;
- hybridization temperature (HT) and wash temperature (WT) for the nucleic acids of the invention defined for the nucleic acids of the invention defined by X–Y: i.e. by the sequence extending from the extremity constituted by the nucleotide at position (X) to the extremity constituted by the nucleotide at position (Y) represented on FIG. 1:

(150)–(287) HT=WT=65° C.
(224)–(287) HT=WT=60° C.
(150)–(1169) HT=WT=70° C.
(1)–(1169) HT=WT=70° C.
(224)–(1169) HT=WT=70° C.
(288)–(1169) HT=WT=70° C.

The invention relates also to the polypeptides coded by the nucleic acids of the invention above defined.

Advantageous polypeptides of the invention contain at least one of the following amino acid sequences in their polypeptide chain:

the one extending from the extremity constituted by amino acid at position (–46) to the extremity constituted by amino acid at position (–1) represented on FIG. 1, or the one extending from the extremity constituted by amino acid at position (–21) to the extremity constituted by amino acid at position (–1) represented on FIG. 1, or SQSNGQNY (SEQ ID NO:4), or
PMVQIPRLVA (SEQ ID NO:5), or
GLTLRTNQTFRDTYAADGGRNG (SEQ ID NO:6), or
PPAAPAAPAA (SEQ ID NO:7), or are constituted by the above-mentioned polypeptide sequences.

The invention also relates to polypeptides containing, in their polypeptide chain, the following amino acid sequence:

SQSNGQNY (SEQ ID NO:4)
and possibly the amino acid sequence
GWDINTPA (SEQ ID NO:13)
and possibly the amino acid sequence
FSRPGLPVEYLQVP (SEQ ID NO:8)
and containing not the amino acid sequence
ACGKAGCQ (SEQ ID NO:14)
and not the amino acid sequence
ACGKAGCT (SEQ ID NO:15)

Advantageous polypeptides of the invention contain in their polypeptide chain the following amino acid sequences:

SQSNGQNY (SEQ ID NO:4)
GWDINTPA (SEQ ID NO:13)
FSRPGLPVEYLQVP (SEQ ID NO:8)
and one at least of the following amino acid sequences:
PMVQIPRLVA (SEQ ID NO:5),
GLTIRTNQTFRDTYAADGGRNG (SEQ ID NO:6),
PPAAPAAPAA (SEQ ID NO:7),
and containing not the amino acid sequence
ACGKAGCQ (SEQ ID NO:14)
and not the amino acid sequence
ACGKAGCT (SEQ ID NO:15).

The following polypeptides are new:
SQSNGQNY (SEQ ID NO:4),
PMVQIPRLVA (SEQ ID NO:5),
GLTLRTNQTFRDTYAADGGRNG (SEQ ID NO:6),
PPAAPAAPAA (SEQ ID NO:7).

Advantageous polypeptides of the invention are liable to react selectively with human sera from tuberculosis patients and particularly patients developing an evolutive tuberculosis, or liable to be recognized by antibodies also recognizing the polypeptide sequence extending from the extremity constituted by amino acid at position (1) to the extremity constituted by amino acid at position (294) represented on FIG. 1, or liable to generate antibodies recognizing the polypeptidic sequence extending from the extremity constituted by amino acid at position (1) to the extremity constituted by amino acid at position (294) represented on FIG. 1.

The invention also includes the peptidic sequences resulting from the modification by substitution and/or by addition and/or by deletion of one or several amino acids in the above defined polypeptides and peptides in so far as this modification does not alter the following properties:

selective reaction with human sera from tuberculosis patients and particularly patients developing an evolutive tuberculosis, and/or reaction with antibodies raised against the amino acid sequence extending from the extremity constituted by amino acid at position (1), to the extremity constituted by amino acid at position (294) represented on FIG. 1.

Advantageous polypeptides of the invention contain or are constituted by one of the above-mentioned polypeptide sequences, and are about 30 to about 35 kD and are preceded by a signal peptide.

Advantageous polypeptides of the invention contain in their polypeptide chain, one at least of the following amino acid sequences or are constituted by one of the following amino acid sequences:

the one extending from the extremity constituted by amino acid at position (1) to the extremity constituted by amino acid at position (294) represented on FIG. 1, the one extending from the extremity constituted by amino acid at position (–46) to the extremity constituted by amino acid at position (294) represented on FIG. 1, the one extending from the extremity constituted by amino acid at position (–21) to the extremity constituted by amino acid at position (294) represented on FIG. 1, the one extending from the extremity constituted by amino acid at position (–46) to the extremity constituted by amino acid at position (–1) represented on FIG. 1, the one extending from the extremity constituted by amino acid at position (–21) to the extremity constituted by amino acid at position (–1) represented on FIG. 1.

It goes without saying that the free reactive functions which are present in some of the amino acids, which are part of the constitution of the polypeptides of the invention, particularly the free carboxyl groups which are carried by the groups Glu or Asp or by the C-terminal amino acid on the one hand and/or the free $NH_2$ groups carried by the N-terminal amino acid or by amino acid inside the peptidic chain, for instance Lys, on the other hand, can be modified insofar as this modification does not alter the above-mentioned properties of the polypeptide.

The molecules which are thus modified are naturally part of the invention. The above-mentioned carboxyl groups can be acylated or esterified.

Other modifications are also part of the invention. Particularly, the amine or ester functions or both of terminal amino acids can be themselves involved in the bond with other amino acids. For instance, the N-terminal amino acid can be linked to a sequence comprising from 1 to several amino acids corresponding to a part of the C-terminal region of another peptide.

The polypeptides according to the invention can be glycosylated or not, particularly in some of their glycosylation sites of the type Asn-X-Ser or Asn-X-Thr, X representing any amino acid.

Other advantageous polypeptides of the invention consist in one of the following amino acid sequences:

the one extending from the extremity constituted by amino acid at position (-46) to the extremity constituted by amino acid at position (-1) represented on FIG. 1, or the one extending from the extremity constituted by amino acid at position (-21) to the extremity constituted by amino acid at position (-1) represented on FIG. 1.

These polypeptides can be used as signal peptides, the role of which is to initiate the translocation of a protein from its site of synthesis to the membrane and which is excised during translocation.

Advantageous polypeptides of the invention are the ones constituted by:

SQSNGQNY (SEQ ID NO:4),

PMVQIPRLVA (SEQ ID NO:5),

GLTRTNQTFRDTYAADGGRNG (SEQ ID NO:6),

PPAAPAAPAA (SEQ ID NO:7), the one extending from the extremity constituted by amino acid at position (1) to the extremity constituted by amino acid at position (294) represented on FIG. 1, the one extending from the extremity constituted by amino acid at position (-46) to the extremity constituted by amino acid at position (294) represented on FIG. 1, the one extending from the extremity constituted by amino acid at position (-21) to the extremity constituted by amino acid at position (294) represented on FIG. 1, the one extending from the extremity constituted by amino acid at position (-46) to the extremity constituted by amino acid at position (-1) represented on FIG. 1, the one extending from the extremity constituted by amino acid at position (-21) to the extremity constituted by amino acid at position (-1) represented on FIG. 1.

All these polypeptides are new.

Figure 2A:
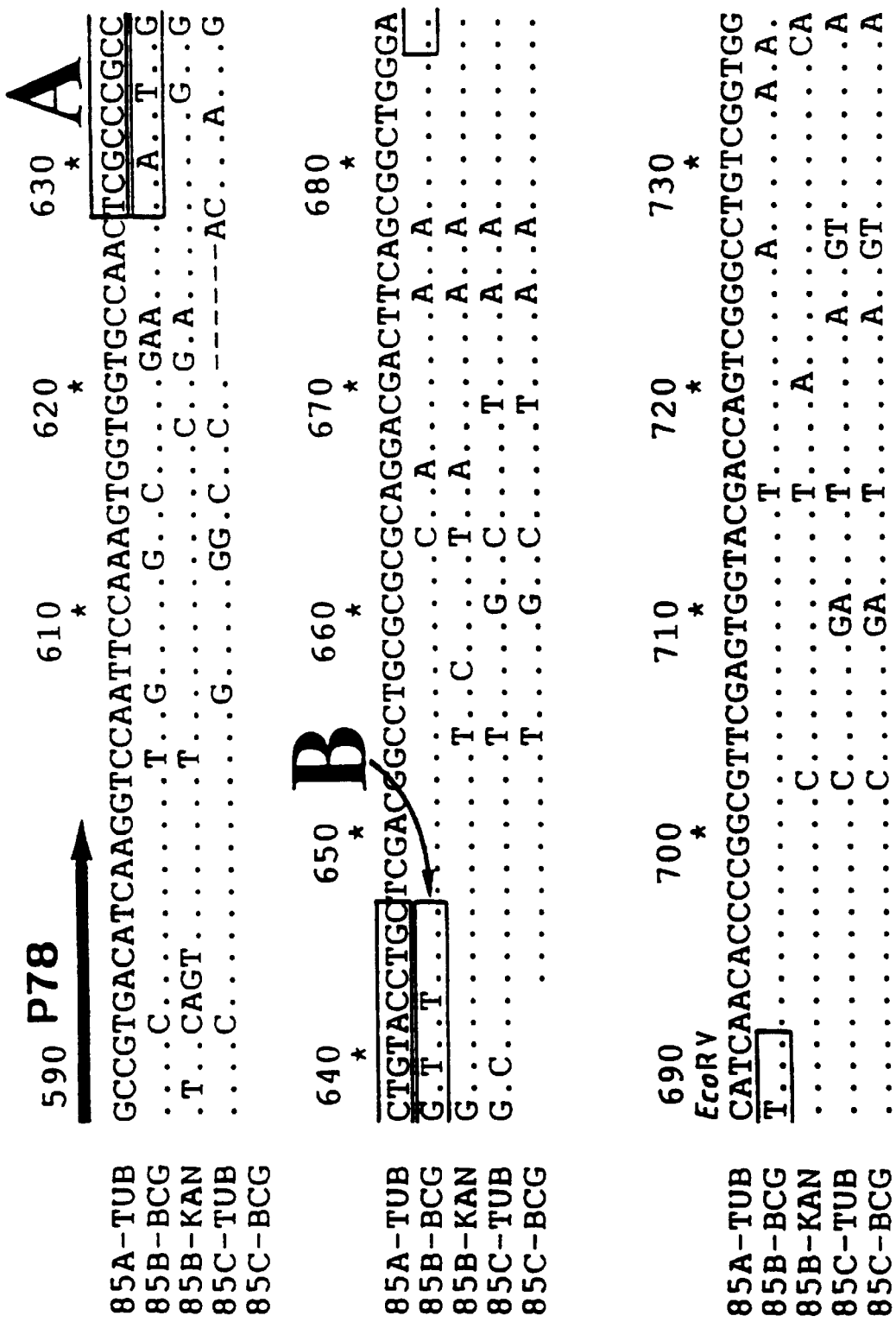

Other interesting polypeptides, which are common to the already known sequences of antigens 85A, 85B and 85C of *M. tuberculosis, M. bovis* and *M. kansasii* are (see FIG. 2A)

GWDINTPA (SEQ ID NO:13), and

FSRPGLPVEYLQVP (SEQ ID NO:8).

It is to be noted that the above-mentioned polypeptides are derived from the expression products of a DNA derived, as explained hereafter in the examples, from the nucleotide sequence coding for a protein of 33-kDa secreted by *Mycobacterium tuberculosis* or from the partial nucleotide sequence coding for a protein of 33-kDa secreted by *M. bovis BCG*, or from related nucleotide sequences which will be hereafter designated by 85C genes.

The invention also relates to the amino acid sequences constituted by the above-mentioned polypeptides and a protein or an heterologous sequence with respect to said polypeptide, said protein or heterologous sequence comprising for instance from about 1 to about 1000 amino acids. These amino acid sequences will be called fusion proteins.

In an advantageous fusion protein of the invention, the heterologous protein is β-galactosidase.

The invention also relates to any recombinant nucleic acids containing at least one of the nucleic acids of the invention inserted in a heterologous nucleic acid.

The invention relates more particularly to recombinant nucleic acid such as defined, in which the nucleotide sequence of the invention is preceded by a promoter (particularly an inducible promoter) under the control of which the transcription of said sequence is liable to be processed and possibly followed by a sequence coding for transcription termination signals.

The invention also relates to the recombinant nucleic acids in which the nucleic acid sequences coding for the polypeptide of the invention and possibly the signal peptide, are recombined with control elements which are heterologous with respect to the ones to which they are normally associated with in the mycobacterial genome, more particularly, the regulation elements adapted to control their expression in the cellular host which has been chosen for their production.

The invention also relates to recombinant vectors, particularly for cloning and/or expression, comprising a vector sequence, notably of the type plasmid, cosmid or phage DNA or virus DNA, and a recombinant nucleic acid of the invention, in one of the non-essential sites for its replication.

According to an advantageous embodiment of the invention, the recombinant vector contains, in one of its non-essential sites for its replication, necessary elements to promote the expression of polypeptides according to the invention in a cellular host and notably a promoter recognized by the RNA polymerase of the cellular host, particularly an inducible promoter and possibly a sequence coding for transcription termination signals and possibly a signal sequence and/or an anchor sequence.

According to another additional embodiment of the invention, the recombinant vector contains the elements enabling the expression by *E. coli* of a nucleic acid according to the invention inserted in the vector, and particularly the elements enabling the expression of the gene or part thereof of β-galactosidase.

The invention also relates to a cellular host which is transformed by a recombinant vector according to the invention, and containing the regulation elements enabling the expression of the nucleotide sequence coding for the polypeptide according to the invention in this host.

The invention also relates to a cellular host chosen from among bacteria such as *E. coli*, transformed by a vector as defined above, or chosen from among eukaryotic organism, such as CHO cells or insect cells, transfected by a vector as above defined.

The invention relates to an expression product of a nucleic acid expressed by a transformed cellular host according to the invention.

The invention also relates to the use of any secreted polypeptide of the invention as a carrier antigen for foreign epitopes (epitopes of a polypeptide sequence heterologous with respect to the polypeptides of the invention) in the *Mycobacterium bovis BCG* vaccine strain.

The *Mycobacterium bovis BCG* vaccine strain used can be available from Institut Pasteur (Paris), under 1173$P_2$.

The recombinant DNA comprising the nucleic acid coding for anyone of the polypeptides of the invention and the nucleic acid coding for any foreign epitopes as defined above, can contain. the promoter sequence of said polypeptide of the invention, the signal sequence of said polypeptide, possibly the coding part of said polypeptide and the coding nucleic acid of the foreign epitope, said nucleic acid of the foreign epitope being for instance either directly located after the signal sequence, and if the coding part of the the polypeptide of the invention is present, upstream from the coding part of the polypeptide of the invention, or located downstream from the coding part of the polypeptide of the invention, or located within the coding part of the polypeptide of the invention.

The recombinant DNA as above defined can be transformed into the vaccine strain BCG where it leads to the expression and secretion of a recombinant protein antigen.

From the nucleic acids of the invention, probes (i.e. cloned or synthetic oligonucleotides) can be inferred.

These probes can be from 15 to the maximum number of nucleotides of the selected nucleic acids. The oligonucleotides can also be used either as amplification primers in the PCR technique (PCR, Mullis and Faloona, Methods in Enzymology, vol. 155, p. 335, 1987) to generate specific enzymatically amplified fragments and/or as probes to detect fragments amplified between bracketing oligonucleotide primers.

The specificity of a PCR-assisted hybridization assay can be controlled at different levels.

The amplification process or the detection process or both can be specific. The latter case giving the higher specificity is preferred.

The invention also relates to a process for preparing a polypeptide according to the invention comprising the following steps:

the culture in an appropriate medium of a cellular host which has previously been transformed by an appropriate vector containing a nucleic acid according to the invention, the recovery of the polypeptide produced by the above said transformed cellular host from the above said culture, and the purification of the polypeptide produced, eventually by means of immobilized metal ion affinity chromatography (IMAC).

The polypeptides of the invention can be prepared according to the classical techniques in the field of peptide synthesis.

The synthesis can be carried out in homogeneous solution or in solid phase.

For instance, the synthesis technique in homogeneous solution which can be used is the one described by Houben-weyl in the book entitled "Methode der organischen chemie" (Method of organic chemistry) edited by E. Wunsh, vol. 15-I et II. THIEME, Stuttgart 1974.

The polypeptides of the invention can also be prepared in solid phase according to the methods described by Atherton and Shepard in their book entitled "Solid phase peptide synthesis" (IRL Press, Oxford, New York, Tokyo, 1989).

The invention also relates to a process for preparing the nucleic acids according to the invention.

A suitable method for chemically preparing the single-stranded nucleic acids (containing at most 100 nucleotides of the invention) comprises the following steps:

DNA synthesis using the automatic β-cyanoethyl phosphoramidite method described in Bioorganic Chemistry 4; 274–325, 1986.

In the case of single-stranded DNA, the material which is obtained at the end of the DNA synthesis can be used as such.

A suitable method for chemically preparing the double-stranded nucleic acids (containing at most 100 bp of the invention) comprises the following steps:

DNA synthesis of one sense oligonucleotide using the automatic β-cyanoethyl phosphoramidite method described in Bioorganic Chemistry 4; 274–325, 1986, and DNA synthesis of one anti-sense oligonucleotide using said above-mentioned automatic β-cyanoethyl phosphoramidite method, combining the sense and anti-sense oligonucleotides by hybridization in order to form a DNA duplex, cloning the DNA duplex obtained into a suitable plasmid vector and recovery of the DNA according to classical methods, such as restriction enzyme digestion and agarose gel electrophoresis.

A method for the chemical preparation of nucleic acids of length greater than 100 nucleotides—or base pairs, in the case of double-stranded nucleic acids comprises the following steps:

assembling of chemically synthesized oligonucleotides, provided at their ends with different restriction sites, the sequences of which are compatible with the succession of amino acids in the natural peptide, according to the principle described in Proc. Nat. Acad. Sci. USA 80; 7461–7465, 1983, cloning the DNA thereby obtained into a suitable plasmid vector and recovery of the desired nucleic acid according to classical methods, such as restriction enzyme digestion and agarose gel electrophoresis.

The invention also relates to antibodies themselves formed against the polypeptides according to the invention.

It goes without saying that this production is not limited to polyclonal antibodies.

It also relates to any monoclonal antibody produced by any hybridoma liable to be formed according to classical methods from splenic cells of an animal, particularly of a mouse or rat, immunized against the purified polypeptide of the invention on the one hand, and of cells of a myeloma cell line on the other hand, and to be selected by its ability to produce the monoclonal antibodies recognizing the polypeptide which has been initially used for the immunization of the animals.

The invention also relates to any antibody of the invention labeled by an appropriate label of the enzymatic, fluorescent or radioactive type.

The peptides which are advantageously used to produce antibodies, particularly monoclonal antibodies, are the following ones listed in Table 1 (referring to FIG. 1):

TABLE 1

| | | |
|---|---|---|
| 38 | $H_2$N-DGLRAQDDYNGWDINTPAFE-COOH | 57 (SEQ ID NO:16) |
| 78 | $H_2$N-TDWYQPSQSNGQNYTYKWET-COOH | 97 (SEQ ID NO:17) |
| 174 | $H_2$N-ANSMWGPSSDPAWKRNDPMV-COOH | 193 (SEQ ID NO:18) |
| 204 | $H_2$N-RIWVYCGNGTPSDLGGDNIP-COOH | 223 (SEQ ID NO:19) |
| 235 | $H_2$N-NQTFRDTYAADGGRNGVFNF-COOH | 254 (SEQ ID NO:20) |
| 250 | $H_2$N-GVFNFPPNGTHSWPYWNEQL-COOH | 269 (SEQ ID NO:21) |
| 275 | $H_2$N-DIQHVLNGATPPAAPAAPAA-COOH | 294 (SEQ ID NO:22) |

The amino acid sequences are given in the one-letter code.

Variations of the peptides listed in Table 1 are also possible depending on their intended use. For example, if the peptides are to be used to raise antisera, the peptides may be synthesized with an extra cysteine residue added. This extra cysteine residue is preferably added to the amino terminus and facilitates the coupling of the peptide to a carrier protein which is necessary to render the small peptide immunogenic. If the peptide is to be labeled for use in radioimmunoassays, it may be advantageous to synthesize the protein with a tyrosine attached to either the amino or carboxyl terminus to facilitate iodination. These peptides therefore possess the primary sequence of the peptides listed in Table 1 but with additional amino acids which do not appear in the primary sequence of the protein and whose sole function is to confer the desired chemical properties to the peptides.

The invention also relates to any polypeptide according to the invention labeled by an appropriate label of the enzymatic, fluorescent, radioactive type.

The invention also relates to a process for detecting in vitro antibodies related to tuberculosis in a human biological sample liable to contain them, this process comprising contacting the biological sample with a polypeptide or a peptide according to the invention under conditions enabling an in vitro immunological reaction between said polypeptide and the antibodies which are possibly present in the biological sample and the in vitro detection of the antigen/antibody complex which may be formed.

Preferably, the biological medium is constituted by a human serum.

The detection can be carried out according to any classical process.

By way of example, a preferred method brings into play an immunoenzymatic process according to an ELISA, immunofluorescent, or radioimmunological (RIA) technique, or the equivalent ones.

Such a method for detecting in vitro antibodies related to tuberculosis comprises for instance the following steps:

deposit of determined amounts of a polypeptidic composition according to the invention in the wells of a titration microplate, introduction into said wells of increasing dilutions of the serum to be diagnosed, incubation of the microplate, repeated rinsing of the microplate, introduction into the wells of the microplate of labeled antibodies against the blood immunoglobulins, the labeling of these antibodies being based on the activity of an enzyme which is selected from among the ones which are able to hydrolyze a substrate by modifying the absorption of the radiation of this latter at least at a given wavelength, detection by comparison with a control standard of the amount of hydrolyzed substrate.

The invention also relates to a process for detecting and identifying in vitro antigens of *M. tuberculosis* in a human biological sample liable to contain them, this process comprising:

contacting the biological sample with an appropriate antibody of the invention under conditions enabling an in vitro immunological reaction between said antibody and the antigens of *M. tuberculosis* which are possibly present in the biological sample and the in vitro detection of the antigen/antibody complex which may be formed.

Preferably, the biological medium is constituted by sputum, pleural effusion liquid, broncho-alveolar washing liquid, urine, biopsy or autopsy material.

The invention also relates to an additional method for the in vitro diagnosis of tuberculosis in a patient liable to be infected by *Mycobacterium tuberculosis* comprising the following steps:

the possible previous amplification of the amount of the nucleotide sequences according to the invention, liable to be contained in a biological sample taken from said patient by means of a DNA primer set as defined above, contacting the above-mentioned biological sample with a nucleotide probe of the invention, under conditions enabling the production of an hybridization complex formed between said probe and said nucleotide sequence, detecting the above said hybridization complex which has possibly been formed.

To carry out the in vitro diagnostic method for tuberculosis in a patient liable to be infected by *Mycobacterium tuberculosis* as defined above, the following necessary or kit can be used, with said necessary or kit comprising:

a determined amount of a nucleotide probe of the invention, advantageously the appropriate medium for creating an hybridization reaction between the sequence to be detected and the above mentioned probe, advantageously, reagents enabling the detection of the hybridization complex which has been formed between the nucleotide sequence and the probe during the hybridization reaction.

The invention also relates to an additional method for the in vitro diagnosis of tuberculosis in a patient liable to be infected by *Mycobacterium tuberculosis* comprising:

contacting a biological sample taken from a patient with a polypeptide or a peptide of the invention, under conditions enabling an in vitro immunological reaction between said polypeptide or peptide and the antibodies which are possibly present in the biological sample and the in vitro detection of the antigen/antibody complex which has possibly been formed.

To carry out the in vitro diagnostic method for tuberculosis in a patient liable to be infected by *Mycobacterium tuberculosis*, the following necessary or kit can be used, with said necessary or kit comprising:

a polypeptide or a peptide according to the invention, reagents for making a medium appropriate for the immunological reaction to occur, reagents enabling to detect the antigen/antibody complex which has been produced by the immunological reaction, with said reagents possibly having a label, or being liable to be recognized by a labeled reagent, more particularly in the case where the above-mentioned polypeptide or peptide is not labeled.

The invention also relates to an additional method for the in vitro diagnosis of tuberculosis in a patient liable to be infected by *M. tuberculosis*, comprising the following steps:

contacting the biological sample with an appropriate antibody of the invention under conditions enabling an in vitro immunological reaction between said antibody and the antigens of *M. tuberculosis* which are possibly present in the biological sample and the in vitro detection of the antigen/antibody complex which may be formed.

To carry out the in vitro diagnostic method for tuberculosis in a patient liable to be infected by *Mycobacterium*

*tuberculosis*, the following necessary or kit can be used, with said necessary or kit comprising:

an antibody of the invention, reagents for making a medium appropriate for the immunological reaction to occur, reagents enabling the detection of the antigen/antibody complexes which have been produced by the immunological reaction, with said reagent possibly having a label or being liable to be recognized by a labeled reagent, more particularly in the case where the above-mentioned antibody is not labeled.

An advantageous kit for the in vitro diagnosis of tuberculosis comprises:

at least a suitable solid phase system, e.g. a microtiterplate for deposition thereon of the biological sample to be diagnosed in vitro, a preparation containing one of the monoclonal antibodies of the invention, a specific detection system for said monoclonal antibody, appropriate buffer solutions for carrying out the immunological reaction between the biological sample and said monoclonal antibody on the one hand, and the bonded monoclonal antibodies and the detection system on the other hand.

The invention also relates to a kit, as described above, also containing a preparation of one of the polypeptides or peptides of the invention, with said antigen of the invention being either a standard (for quantitative determination of the antigen of *M. tuberculosis* which is sought) or a competitor, with respect to the antigen which is sought, for the kit to be used in a competition dosage process.

The invention also relates to a necessary or kit for the diagnosis of prior exposure of a subject to *M. tuberculosis*, with said necessary or kit containing a preparation of at least one of the polypeptides or peptides of the invention, with said preparation being able to induce in vivo, after being intradermally injected to a subject, a delayed-type hypersensitivity reaction at the site of injection, in case the subject has had prior exposure to *M. tuberculosis.*

This necessary or kit is called a skin test.

The invention also relates to an immunogenic composition comprising a polypeptide or a peptide according to the invention, in association with a pharmaceutically acceptable vehicle.

The invention also relates to a vaccine composition comprising among other immunogenic principles any one of the polypeptides or peptides of the invention or the expression product of the invention, possibly coupled to a natural protein or to a synthetic polypeptide having a sufficient molecular weight so that the conjugate is able to induce in vivo the production of antibodies neutralizing *Mycobacterium tuberculosis*, or induce in vivo a cellular immune response by activating *M. tuberculosis* antigen-responsive T cells.

The peptides of the invention which are advantageously used as immunogenic principle are the ones mentioned in Table 1.

Other characteristics and advantages of the invention will appear in the following examples and the figures illustrating the invention.

MATERIALS AND METHODS

1. Preparation of genomic DNA (Thole J. et al., 1985, "Cloning of *Mycobacterium bovis BCG* DNA and expression of antigens in *Escherichia coli*" Infect. Immun. 50:3800):

*M. bovis BCG* was cultivated at 37° C. in Sauton medium and harvested after an additional incubation of 18 h in the presence of 1% glycine added at the end of the late exponential growth phase. The bacteria were treated with lysozyme and proteinase K, lysed with sodium dodecyl sulfate, phenol extracted and ethanol precipitated.

2. Genomic libraries:

A λgtll recombinant library constructed from genomic DNA of *M. tuberculosis* (Erdman strain), was obtained from Young R. A. et al., 1985, "Dissection of *Mycobacterium tuberculosis* antigens using recombinant DNA" Proc. Natl. Acad. Sci. USA 82:2583.

A second λgtll recombinant library was prepared with genomic DNA from *M. bovis BCG* (De Wit L. et al., 1990, "Nucleotide sequence of the 32 kDa-protein gene (antigen 85A) of *Mycobacterium bovis BCG*" Nucl. Ac. Res. 18:3995).

3. Oligonucleotides:

Oligonucleotides were synthesized on an Applied Biosystems DNA synthesizer model 381A, purified on OPC-cartridges (Applied Biosystems), lyophilized and dissolved in TE buffer (10 mM Tris-HCl, pH 7,4).

$^{32}$p labeling of the oligonucleotides was as described in Sambrook J. et al., 1989, "Molecular Cloning: a Laboratory Manual" Cold Spring Harbor Laboratory, Cold Spring Harbor, N.Y.

4. PCR:

50 ng of *Mycobacterium bovis BCG* DNA was amplified in a 50-μl reaction mixture containing 1 x PCR-buffer (Amersham), 200 μM dNTP, 1 μM each of sense P78 (5'CCGGAATTCATGGGCCGTGACATCAAG) (SEQ ID NO:33) and antisense P79 (5'CCGGAATTCGGTCTCCCACTTGTAAGT) (SEQ ID NO:34) oligonucleotide primers (the location of these two primers is indicated in FIG. 2A. To both oligonucleotides were added an EcoRI sequence preceded by 3 additional nucleotides), and 2 units of Taq DNA polymerase. After denaturation for 90 seconds at 94° C. the reaction was submitted to 40 cycles consisting of 1 minute at 93° C. (denaturation), 90 seconds at 55° C.(annealing), 2 minutes at 72° C. (extension), followed by a 5 minute final extension at 72° C. After extraction with 150 μl chloroform, the amplified DNA was washed three times with 0.75 ml $H_2O$ in a Centricon-30 for 6 minutes at 6500 rpm in the Sorvall SS 34 rotor. After digestion with EcoRI the DNA was ligated into EcoRI-digested, phosphatase-treated Bluescribe-M13+ vector. DH5α *E. coli* (Gibco-BRL) were transformed and plated on Hybond-N filters. Colonies were selected by hybridization with $^{32}$P-labeled oligonucleotide probe-A (5'-TCGCCCGCCCTGTACCTG) (SEQ ID NO:35) and oligonucleotide probe-B (5'-TCACCTGCGGTTTATCTG) (SEQ ID NO:36). Hybridization and washing conditions for the oligonucleotides were as described by Jacobs et al. (Jacobs et al., 1988, "The thermal stability of oligonucleotide duplexes is sequence independent in tetraalkylammonium salt solutions: application to identifying recombinant DNA clones" Nucl. Acid Res. 16:4637).

5. Screening of the λgt11 *M. tuberculosis* and *Mycobacterium bovis BCG* recombinant DNA libraries:

The two λgt11 recombinant libraries were screened by colony hybridization (Sambrook J. et al., 1989, "Molecular Cloning: a Laboratory Manual" Cold Spring Harbor Laboratory, Cold Spring Harbor, N.Y.) with a 800 bp HindIII fragment of the previously cloned gene 85A (Borremans L. et al., 1989, "Cloning, sequence determination and expression of a 32-kilodalton protein gene of *Mycobacterium tuberculosis*" Infect. Immun. 57:3123) which does not discriminate gene 85A from 85B (see FIGS. 2A and 4A). Twelve positive *M. tuberculosis* and 12 *Mycobacterium bovis BCG* plaques were retained and screened by hybridization with $^{32}$P-labeled oligonucleotide-probe C (5'-TCGCAGAGCAACGGCCAGAACTAC) (SEQ ID NO:37) as described above.

From the *M. tuberculosis* λgt11 library, one selected bacteriophage #11 was partially digested with EcoRI and its 5 kbp insert was subcloned in Bluescribe-M13+. From this recombinant plasmid named 11-2, a 3,500 bp BamHI-EcoRI fragment was subcloned in M13-mp18 and M13-mp19 (Sambrook J. et al., 1989, "Molecular Cloning: a Laboratory Manual" Cold Spring Harbor Laboratory, Cold Spring Harbor, N.Y.).

6. Recombinant DNA analysis:

It was as described in Borremans L. et al., 1989, "Cloning, sequence determination and expression of a 32-kilodalton protein gene of M*ycobacterium tuberculosis*" Infect. Immun. 57:3123.

7. Sequencing:

Sequence analysis was done by the primer extension dideoxy termination method of Sanger et al. (Sanger F. et al., 1977, "DNA sequencing with chain termination inhibitors" Proc. Natl. Acad. Sci. USA 74:5463) after subcloning of specific fragments in Bluescribe-M13+(Chen E. J. et al., 1985, "Supercoil sequencing: a fast simple method for sequencing plasmid DNA" DNA 4:165) or in mp18 and mp19 M13 vectors. Sequence analysis was greatly hampered by the high GC content of the *M. tuberculosis* DNA (65%). Sequencing reactions were therefore performed with several DNA polymerases according to manufacturers protocols: T7 DNA polymerase ("Sequenase" USB), T7 DNA polymerase (Pharmacia), and Taq DNA polymerase (Promega) using 7-deaza-dGTP instead of dGTP. Several oligodeoxynucleotides were synthesized and used to focus on ambiguous regions of the sequence. The sequencing strategy is summarized in FIG. 1.

8. Sequence comparison and analysis:

Routine computer-aided analysis of the nucleic acid and deduced amino acid sequences were performed with the LGBC program from Bellon B., 1988, "Apple Macintosh programs for nucleic and protein sequence analysis" Nucleic Acid Res. 16:1837. Homology searches used the FASTA programs from Pearson W. R. et al., 1988, "Improved tools for biological sequence comparison" Proc. Natl. Acad. Sci. USA 85:2444, and the various DNA and protein data bank from the EMBL-server facilities. Multiple alignments were obtained with 'Align 1.01' (Scientific and Educational Software).

9. Southern blot analysis:

Genomic DNA from *Mycobacterium bovis BCG* was completely digested with SphI, EcoRI or KpnI, electrophoresed on a 1% agarose gel, transferred to Hybond-N filter (Amersham) after denaturation and neutralization and either hybridized with $^{32}$P-labeled-oligonucleotide probes (A, B, C) in the conditions described in Jacobs et al., 1988, "The thermal stability of oligonucleotide duplexes is sequence independent in tetraalkylammonium salt solutions: application to identifying recombinant DNA clones" Nucl. Ac. Res. 16:4637, or random-primed $^{32}$P-labeled DNA restriction fragments that were found to discriminate the 3 genes 85A, 85B, and 85C.

Probe 85A was a 230 bp PstI fragment from plasmid BY-5 (Borremans L. et al., 1989, "Cloning, sequence determination and expression of a 32-kilodalton protein gene of *Mycobacterium tuberculosis*" Infect. Immun. 57:3123 and FIG. 2A). Probe 85B was a 400 bp SmaI-EcoRV fragment from a 85B recombinant plasmid named 5.1, derived from our *Mycobacterium bovis BCG* λgt11 library, whose map is presented in FIG. 4A (see also FIG. 2A). Probe 85C was a 280 bp SmaI-kpnI fragment from plasmid 11.2 (see also FIG. 4A and 2A).

These DNA fragments were prepared by gel electrophoresis on low melting point agarose followed by a rapid purification on Qiagen (marketed by: Westburg, Netherlands) (tip 5) according to manufacturers protocol and labeled in the presence of α-$^{32}$P-dCTP (Feinberg A. P. et al., 1983, "A technique for radiolabeling DNA restriction endonuclease fragments to high specific activity" Anal. Biochem. 132:6).

10. Pulse Field electrophoresis DNA separation:

DNA preparation, restriction enzyme digestion and pulse-field gel electrophoresis were performed as described by Vincent Levy-Frebault V. et al., 1990, ("DNA polymorphism in *Mycobacterium paratuberculosis*, "wood pigeon mycobacteria" and related mycobacteria analyzed by field inversion gel electrophoresis", J. Clin. Microbiol. 27:2723). Briefly cells from fresh cultures were mixed with 1% low-melting-point agarose (v/v) and submitted to successive treatments with zymolase (Seikagaki Kogyo, Tokyo, Japan), lysozyme, and sodium dodecyl sulfate in the presence of proteinase K (Boehringer GmbH, Mannheim, Germany). After inactivation of proteinase K with phenylmethylsulfonyl fluoride (Bio-Rad Laboratories), agarose blocks were digested overnight with 50 U of DraI (Bio-Rad Laboratories). Then blocks were loaded into a 1% agarose gel prepared and electrophoresed in 0.66 TBE (Tris-boric acid—EDTA). Field inversion gel electrophoresis was carried out using a Dnastar Pulse (Dnastar, USA) apparatus. Forward and reverses pulses were set at 0.33 sec and 0.11 sec at the beginning of the run and 60 sec and 20 sec (or 30 sec and 10 sec) at the end of the run depending on the molecular weight zone to be expanded. The run time was set at 36 h, the voltage used was 100 V and producing about 325 mA and temperature was maintained at 18° C. Lambda concatemers were used as molecular weight markers. At the end of the run, the gels were stained with ethidium bromide, photographed under UV light and transferred onto nylon membranes according to Maniatis T. et al., 1982, "Molecular cloning: a laboratory manual" Cold Spring Harbor Laboratory, Cold Spring Harbor, N.Y. 545 pp.

RESULTS

1. Cloning of the 85C gene of *M. tuberculosis:*

Since no specific probe or monoclonal antibody was available to detect specifically an 85C or related antigen which was expected to bear extensive homology to gene 85A and gene 85B, this screening required the development of a new procedure. The strategy used was based on the PCR amplification of a 245 bp DNA fragment coding for amino acids 18–98 of the mature antigen 85A chosen because it is surrounded at both ends by highly conserved DNA sequences when the sequences of antigen A and B are aligned (see primers P78 and P79 in FIG. 2A). It was thus supposed that an equivalent homology might exist with the sequence of antigen 85C in the same region.

From *Mycobacterium bovis BCG* genomic DNA, a 245 bp DNA fragment was readily obtained. The latter was purified and subcloned in a Bluescribe M13+vector after digestion with EcoRI. About 80 recombinant plasmid-containing colonies were tested by plating on nylon filters and hybridized under stringent conditions with a labeled synthetic oligonucleotide recognizing either sequence 85A (5'-TCGCCCGCCCTGTACCTG) (SEQ ID NO:35) or sequence 85B (5'-TCACCTGCGGTTTATCTG) (SEQ ID NO:36) within the PCR amplified fragment (see FIG. 2A). Several clones that hybridized with each oligonucleotide probe were sequenced and the sequences were all identical to sequence 85A in the clones hybridizing with oligoprobe A and to sequence 85B for those hybridizing with oligoprobe B. Several of the remaining clones were sequenced and they all showed a marked sequence divergence from 85A and 85B covering a 24-nucleotide stretch which is totally distinct from sequence A and B (FIG. 2A, box marked C) (The homology to sequence B is only 33% in this region). Assuming these inserts might represent an amplified fragment of the 85C gene and that this 24 nucleotide sequence is characteristic of the putative 85C gene, an oligonucleotide probe (oligo 85C) based on this sequence was synthesized.

The latter probe was labeled with $^{32}P$ and used to screen a collection of 24 λgt11 recombinant phages that were selected in our *M. tuberculosis* and *Mycobacterium bovis* BCG λgt11 libraries by hybridization with a 800 bp nonspecific HindIII DNA fragment of the previously cloned gene 85A.

One hybridizing λgt11-*M. tuberculosis* recombinant was retained, characterized by restriction mapping and sequenced.

2. Sequence of the 85C gene of *Mycobacterium tuberculosis*:

The 1211 nucleotide sequence derived from various sequenced fragments is represented in FIG. 1. The DNA sequence contains a 1,020-bp-long open reading frame, starting at position 150 and ending with a TGA codon at position 1170. The common NH2 terminal amino acid sequence of the antigen 85 proteins, Phe-Ser-Arg-ProGly-Leu (SEQ ID NO:1) (De Bruyn J. et al., 1987, "Purification, partial characterization and identification of a 32 kDa protein antigen of *Mycobacterium bovis* BCG" Microb. Pathogen. 2:351) could be located within this open reading frame from the nucleotide sequence beginning with a TTC codon at position 288 (FIG. 1). Therefore, the DNA region upstream from this sequence is expected to code for a signal peptide required for the secretion of this antigen. The mature protein consists of 294 amino acid residues corresponding to a calculated molecular weight of 32,021.

Interestingly, the N-terminal sequence of the mature protein contains the entire 26 amino acid sequence (phe-ser-arg-pro-gly-leu-pro-val-glu-tyr-leugln-val-pro-ser-ala-ser-met-gly-arg-asp-ile-lys-val gln-phe) (SEQ ID NO:38) described by Wiker H. G. et al., 1990, "Evidence for three separate genes encoding the proteins of the mycobacterial antigen 85 complex" Infect. Immun. 58:272, and which differs only from the common 85B and 85A sequence by an alanine instead of a proline in position 16 of the mature protein. Two ATG codons were found to precede the TTC phenylalanine codon at nucleotide position 288 (FIG. 1) in the same reading frame. Use of these two ATG would lead to the synthesis of signal peptides of either 21 or 46 amino acid residues (the latter situation has been represented in FIG. 1 for reasons indicated below).

The base composition of antigen 85C gene was identical to that of the 85A gene with an overall G-C composition of 64.57% and a strong preference for G or C in codon position 3 (average 85%). In contrast to antigen 85A and 85B that contain 3 cysteins, the sequence of antigen 85C shows a single cystein residue at position 254. In fact, the two substituted cysteins are located in the region of the mature 85C protein which contains the largest divergent sequence bloc (FIG. 2B) (SQSNGQNY) (SEQ ID NO:4) (The corresponding DNA sequence was used to synthesize the oligonucleotide probe "C" (see above)). Not surprisingly, this hydrophilic region is also the most divergent when the hydropathy plots of the 3 antigens are compared and thus could be either a variable "epitope" of all 85-antigens and/or a characteristic epitope of antigen 85C since it was also found in antigen 85C from *M. bovis* BCG (FIG. 2B, fifth line).

Another characteristic feature of antigen 85C is the presence of the unusual hydrophobic repetitive proline alanine motive PPAAPAAPAA (SEQ ID NO:7) at the carboxyterminal of the molecule.

Figure 3:
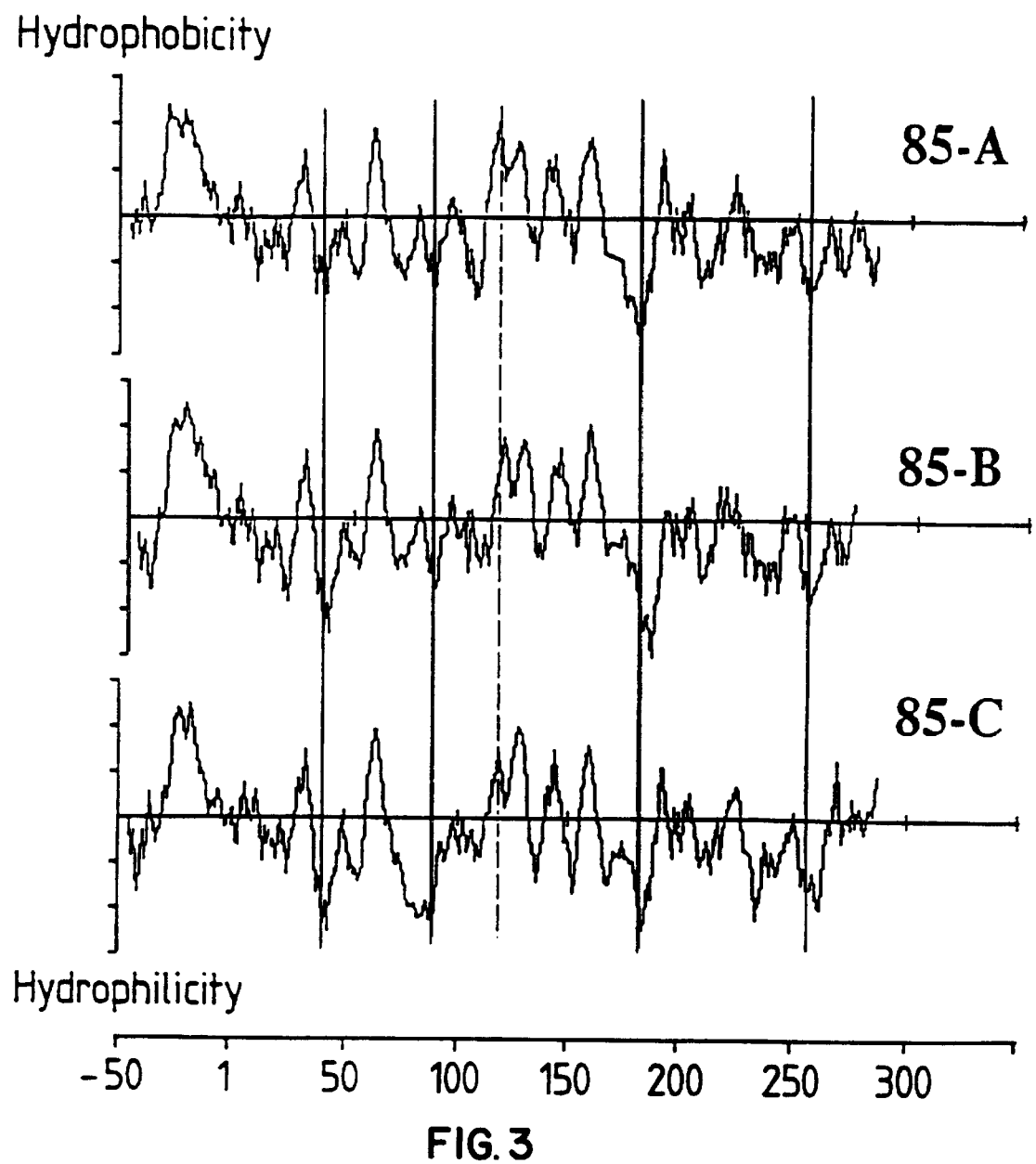

3. Hydropathy pattern:

The hydropathy pattern of *M. tuberculosis* 85C antigen was determined by the method of Kyte and Doolittle (Kyte J. et al., 1982, "Simple method for displaying the hydropathy character of a protein" J. Mol. Biol. 157:105). The octapeptide profiles were compared to antigen 85A and 85B (FIG. 3). As anticipated from the amino acid sequences, the patterns are roughly similar for the three antigens except for some major differences at region 84-92 and in the carboxyterminal part of the three proteins.

4. Sequence homologies:

DNA sequences from antigen 85A (Borremans L. et al., 1989, "Cloning, sequence determination and expression of a 32-kilodalton protein gene of *Mycobacterium tuberculosis*" Infect. Immun. 57:3123; De Wit L. et al., 1990, "Nucleotide sequence of the 32 kDa-protein gene (antigen 85A) of *Mycobacterium bovis* BCG" Nucl. Ac. Res. 18:3995), 85B (Matsuo K. et al., 1988, "Cloning and expression of the *Mycobacterium bovis* BCG gene for extracellular α-antigen" J. Bacteriol. 170:3847; Matsuo et al., 1990, "Cloning and Expression of the gene for cross-reactive α-antigen of *M. kansasii*" Infect. Immunity 58:550–556) and 85C were aligned. An alignment of the three DNA sequences is shown in FIG. 2A. At the DNA level, the homology is maximal between the regions coding for the 3 mature proteins. In this region, the homology between A and B is 77.5% whereas it reaches only 70.8% between the coding regions of genes A and C and 71.9% between B and C, respectively. Beyond nucleotide 1369 of sequence 85A and upstream from nucleotide position 475 (i.e. within the signal sequence and promoter region) there is practically no homology between the 3 sequences. No significant homology was detected to other DNA sequences present in the latest release of GenBank-EMBL.

Homologies at the amino acid level, are presented in the alignment in FIG. 2B, again indicating a higher homology between sequences A and B (80.4%) than between B/C or A/C.

Other comparisons between the 85C antigen and the entire SwissProt-NBRF data bank failed to detect any significant homologies to the 85C antigen amino acid sequence. As for the 85A antigen, the 85C sequence does not contain the RGD motif of fibronectin binding proteins nor does it share any homology to the known fibronectin receptors or to the fibronectin binding protein from *Staphylococcus aureus*.

Comparison of the partial PCR derived DNA sequence of the 85C gene of *M. bovis* BCG 1173P$_2$ with that of *Mycobacterium tuberculosis* shows complete identity including the characteristic region corresponding to synthetic oligonucleotide C (see FIG. 2A).

5. Genome characterization:

In order to confirm the existence of different genes coding for the antigen 85 complex M. bovis BCG genomic DNA was digested with SphI, EcoRI and KpnI and the distribution of radioactive signals was examined in Southern blot after hybridization with three specific oligonucleotide (A, B, C) probes (see Materials and Methods and FIG. 2A). Three clearly distinct patterns were obtained confirming the specificity of these probes. Similar type specific profiles could be obtained with three random-priming-labeled DNA restriction fragments (probe 85A, 230 bp; 85B, 400 bp; 85C 280 bp) which were selected within the promoter signal sequence of the three DNAs (FIGS. 2A and 4A). With these three DNA restriction fragments, additional weak bands are also observed which clearly correspond to cross hybridization of the probes to the other two genes. With probe 85C, an additional KpnI fragment was observed that does not hybridize to the C-oligonucleotide probe. This probably indicates that the corresponding KpnI site is located upstream from this gene. Furthermore the size of the observed restriction fragments are not always exactly as expected from the restriction maps of the corresponding cloned genes. These discrepancies probably correspond to some minor sequence differences (restriction polymorphism) possibly in non coding DNA regions (outside of the DNA coding for the antigen 85) between strain of *M. bovis BCG* and the *M. bovis BCG* (strain Tokyo) and *M. tuberculosis* respectively.

6. Pulse field analysis of *M. tuberculosis* genomic DNA:

When the largest available 85A clone BY-5 was hybridized (FIG. 4A) with oligonucleotide probe B, no positive signal was detected whereas oligonucleotide probe A gave a positive hybridization (not shown). This indicates that gene B is not located within 2–2.5 kb of the 5' and 4.0 kb of the 3' border of gene A (FIG. 4A). To confirm and extend this result, pulse-field separated Dral-digested *M. tuberculosis* genomic DNA was further hybridized with the three specific DNA restriction fragments as probes (85A, 85B and 85C) under stringent conditions.

Eight strains of *M. tuberculosis* were compared showing six different patterns, three of which are illustrated in FIG. 5. For most strains examined, the three probes hybridized to fragments of different sizes. For instance, in *M. tuberculosis* H37Ra, the respective size of the DraI fragments hybridizing with probes 85A, B and C were about 242 kb, 212 kb and 225 kb for strain H37Ra, 403 kb, 212 kb and 104 kb for strain H37Rv and 355 kb, 104 kb and 153 kb for strain "11025". Although various strains show some restriction fragment length polymorphism with restriction endonuclease DraI, the simplest interpretation of these results is that the three antigen 85 genes are distantly located (>100 kb) within the mycobacterial genome.

We claim:

1. An isolated nucleic acid segment comprising a nucleotide sequence selected from the group consisting of:

a nucleotide sequence comprising nucleotides from the nucleotide position (1) to the nucleotide position (149) in SEQ ID NO:2;

a nucleotide sequence coding for a polypeptide extending from the amino acid at position 1 to the amino acid at position 46 in SEQ ID NO: 3;

a nucleotide sequence coding for a polypeptide extending from the amino acid at position 26 to the amino acid at position 46 in SEQ ID NO:3;

a nucleotide sequence coding for peptide SQSNGQNY (SEQ ID NO:4);

a nucleotide sequence coding for peptide PMVQIPRLVA (SEQ ID NO:5);

a nucleotide sequence coding for peptide GLTRTNQT-FRDTYAADGGRNG (SEQ ID NO:6);

a nucleotide sequence coding for peptide PPAAPAAPAA (SEQ ID NO:7); a nucleotide sequence fully complementary to the nucleotide sequences listed above; and a nucleotide sequence corresponding to the nucleotide sequences listed above in which nucleotide T is replaced by nucleotide U.

2. The isolated nucleic acid according to claim 1, comprising a nucleic acid coding for a peptide selected from the group consisting of:

a peptide extending from the amino acid at position 1 to the amino acid at position (−1) 46 in SEQ ID NO:3;

a peptide extending from the amino acid at position 26 to the amino acid at position 1 in SEQ ID NO:3;

a peptide extending from the amino acid at position 1 to the amino acid at position 340 in SEQ ID NO:3;

a peptide extending from the amino acid at position 26 to the amino acid at position 340 in SEQ ID NO:3; and a peptide extending from the amino acid at 47 to the amino acid at position 340 in SEQ ID NO:3.

3. The isolated nucleic acid segment according to claim 1, encoding for a protein, wherein said protein:

reacts selectively with human sera from tuberculosis patients, is recognized by antibodies which recognize the amino acid sequence extending from the amino acid at position 47 to the amino acid at position 340 in SEQ ID NO:3; or generates antibodies which recognize the amino acid sequence extending from the amino acid at position position 47 to the amino acid at position 340 in SEQ ID NO:3.

4. The isolated nucleic acid segment according to claim 1 encoding for a mature protein of about 30 to about 35 kDa and containing a sequence for a signal peptide.

5. A recombinant vector comprising:

a vector sequence, wherein said vector sequence is selected from the group consisting of a plasmid, a cosmid, a phage DNA, and a virus DNA; and a nucleic acid segment according to claim 1, inserted in one of the non-essential sites for replication of said vector sequence.

6. A recombinant vector comprising in one of its non-essential sites for replication elements necessary to promote the expression of the polypeptide or peptide encoded by the nucleic acid segment according to claim 1 in a cellular host and also a promoter recognized by the RNA polymerase of the cellular host.

7. The recombinant vector according to claim 5 comprising elements enabling expression by *E. coli* of the polypeptide or peptide.

8. A *Mycobacterium bovis BCG* vaccine strain transformed with the DNA segment according to claim 1, wherein said nucleic segment further comprises a nucleotide acid sequence encoding a foreign epitope.

9. An isolated host cell which is transformed by a recombinant vector according to claim 6.

10. The isolated host cell according to claim 9, wherein said isolated host cell is a prokaryote or an cukaryotic organism.

11. An isolated nucleic acid segment comprising a nucleotide sequence selected from the following nucleotide sequences:

a nucleotide sequence extending from the nucleotide at position (150) to the nucleotide at position (287) in SEQ ID NO:2;

a nucleotide sequence extending from the nucleotide at position (224) to the nucleotide at position (287) in SEQ ID NO:2;

a nucleotide sequence extending from the nucleotide at position (537) to the nucleotide at position (560) in SEQ ID NO:2;

a nucleotide sequence extending from the nucleotide at position (858) to the nucleotide at position (887) in SEQ ID NO:2;

a nucleotide sequence extending from the nucleotide at position (972) to the nucleotide at position (1037) in SEQ ID NO:2;

a nucleotide sequence extending from the nucleotide at position (1140) to the nucleotide at position (1169) in SEQ ID NO:2;

a nucleotide sequence fully complementary to the nucleotide sequences listed above; and a nucleotide sequence corresponding to the nucleotide sequences listed above in which nucleotide T is replaced by nucleotide U.

* * * * *

UNITED STATES PATENT AND TRADEMARK OFFICE
CERTIFICATE OF CORRECTION

PATENT NO. : 5,955,356
DATED : SEPTEMBER 21, 1999
INVENTOR(S) : CONTENT ET AL.

It is certified that error appears in the above-identified patent and that said Letters Patent is hereby corrected as shown below:

Front page, [73] Assignee: "Ghent" should read --Gent--

Col. 6, line 37: "(SEQ ID NO:7)" should read --(SEQ ID NO:6)--

Col. 7, line 12: "PNVQIPRLVA" should read --PMVQIPRLVA--

Col. 13, line 18: insert --L-- after first occurrence of "T"

Col. 23, line 45: replace "leugln" with --leu-gln--

Col. 26, line 22: "11025" should read --1025--

Col. 57, line 54, claim 2: "(-1) 46" should read --46--

Col. 57, line 56, claim 2: "position 1" should read --position 46--

Col. 58, line 52, claim 8: insert --acid-- after "nucleic"

Col. 58, line 53, claim 8: delete "acid" before "sequence"

Col. 58, line 57, claim 10: "cukaryotic" should read --eukaryotic--

Signed and Sealed this

Eighth Day of May, 2001

Attest:

NICHOLAS P. GODICI

Attesting Officer

Acting Director of the United States Patent and Trademark Office

SEQUENCE LISTING

```
(1) GENERAL INFORMATION:

(iii) NUMBER OF SEQUENCES: 38

(2) INFORMATION FOR SEQ ID NO:1:

(i) SEQUENCE CHARACTERISTICS:
          (A) LENGTH: 6 amino acids
          (B) TYPE: amino acid
          (D) TOPOLOGY: linear (ii) MOLECULE TYPE: protein (vii) IMMEDIATE SOURCE:
          (B) CLONE: NH2-terminal amino acid sequence of Antigen
               85A (xi) SEQUENCE DESCRIPTION: SEQ ID NO:1:

Phe Ser Arg Pro Gly Leu
1               5

(2) INFORMATION FOR SEQ ID NO:2:

(i) SEQUENCE CHARACTERISTICS:
          (A) LENGTH: 1211 base pairs
          (B) TYPE: nucleic acid
          (C) STRANDEDNESS: single
          (D) TOPOLOGY: linear (ii) MOLECULE TYPE: DNA (genomic)

(vii) IMMEDIATE SOURCE:
          (B) CLONE: Nucleotide of 85C antigen containing region
               M. tuberculosis (ix) FEATURE:
          (A) NAME/KEY: CDS
          (B) LOCATION: 150..1169

(xi) SEQUENCE DESCRIPTION: SEQ ID NO:2:
```

```
AGGTGTCCGG GCCGACGCTG AATCGTTAGC CAACCGCGAT CTCGCGCTGC GGCCACGACA      60

TTCGAACTGA GCGTCCTCGG TGTGTTTCAC TCGCCCAGAA CAGATTCGAC CGCGTCGTGC     120

GCAGATGAGA GTTGGGATTG GTAGTAGCT ATG ACG TTC TTC GAA CAG GTG CGA      173
                                Met Thr Phe Phe Glu Gln Val Arg
                                 1                5

AGG TTG CGG AGC GCA GCG ACA ACC CTG CCG CGC CGC GTG GCT ATC GCG      221
Arg Leu Arg Ser Ala Ala Thr Thr Leu Pro Arg Arg Val Ala Ile Ala
     10              15                  20

GCT ATG GGG GCT GTC CTG GTT TAC GGT CTG GTC GGT ACC TTC GGC GGG      269
Ala Met Gly Ala Val Leu Val Tyr Gly Leu Val Gly Thr Phe Gly Gly
 25              30              35                  40

CCG GCC ACC GCG GGC GCA TTC TCT AGG CCC GGT CTT CCA GTG GAA TAT      317
Pro Ala Thr Ala Gly Ala Phe Ser Arg Pro Gly Leu Pro Val Glu Tyr
                 45              50              55

CTG CAG GTG CCA TCC GCG TCG ATG GGC CGC GAC ATC AAG GTC CAG TTC      365
Leu Gln Val Pro Ser Ala Ser Met Gly Arg Asp Ile Lys Val Gln Phe
             60              65              70

CAG GGC GGC GGA CCG CAC GCG GTC TAC CTG CTC GAC GGT CTG CGG GCC      413
Gln Gly Gly Gly Pro His Ala Val Tyr Leu Leu Asp Gly Leu Arg Ala
         75              80              85

CAG GAT GAC TAC AAC GGC TGG GAC ATC AAC ACC CCG GCC TTC GAG GAG      461
Gln Asp Asp Tyr Asn Gly Trp Asp Ile Asn Thr Pro Ala Phe Glu Glu
     90              95             100

TAC TAC CAG TCA GGG TTG TCG GTG ATC ATG CCC GTG GGC GGC CAA TCC      509
Tyr Tyr Gln Ser Gly Leu Ser Val Ile Met Pro Val Gly Gly Gln Ser
105             110             115                 120

AGT TTC TAC ACC GAC TGG TAT CAG CCC TCG CAG AGC AAC GGC CAG AAC      557
Ser Phe Tyr Thr Asp Trp Tyr Gln Pro Ser Gln Ser Asn Gly Gln Asn
                125             130             135

TAC ACC TAC AAG TGG GAG ACC TTC CTT ACC AGA GAG ATG CCC GCC TGG      605
Tyr Thr Tyr Lys Trp Glu Thr Phe Leu Thr Arg Glu Met Pro Ala Trp
            140             145             150

CTA CAG GCC AAC AAG GGC GTG TCC CCG ACA GGC AAC GCG GCG GTG GGT      653
Leu Gln Ala Asn Lys Gly Val Ser Pro Thr Gly Asn Ala Ala Val Gly
        155             160             165

CTT TCG ATG TCG GGC GGT TCC GCG CTG ATC CTG GCC GCG TAC TAC CCG      701
Leu Ser Met Ser Gly Gly Ser Ala Leu Ile Leu Ala Ala Tyr Tyr Pro
    170             175             180

CAG CAG TTC CCG TAC GCC GCG TCG TTG TCG GGC TTC CTC AAC CCG TCC      749
Gln Gln Phe Pro Tyr Ala Ala Ser Leu Ser Gly Phe Leu Asn Pro Ser
185             190             195             200

GAG GGC TGG TGG CCG ACG CTG ATC GGC CTG GCG ATG AAC GAC TCG GGC      797
Glu Gly Trp Trp Pro Thr Leu Ile Gly Leu Ala Met Asn Asp Ser Gly
                205             210             215

GGT TAC AAC GCC AAC AGC ATG TGG GGT CCG TCC AGC GAC CCG GCC TGG      845
Gly Tyr Asn Ala Asn Ser Met Trp Gly Pro Ser Ser Asp Pro Ala Trp
            220             225             230

AAG CGC AAC GAC CCA ATG GTT CAG ATT CCC CGC CTG GTC GCC AAC AAC      893
Lys Arg Asn Asp Pro Met Val Gln Ile Pro Arg Leu Val Ala Asn Asn
        235             240             245

ACC CGG ATC TGG GTG TAC TGC GGT AAC GGC ACA CCC AGC GAC CTC GGC      941
Thr Arg Ile Trp Val Tyr Cys Gly Asn Gly Thr Pro Ser Asp Leu Gly
    250             255             260

GGC GAC AAC ATA CCG GCG AAG TTC CTG GAA GGC CTC ACC CTG CGC ACC      989
Gly Asp Asn Ile Pro Ala Lys Phe Leu Glu Gly Leu Thr Leu Arg Thr
265             270             275             280

AAC CAG ACC TTC CGG GAC ACC TAC GCG GCC GAC GGT GGA CGC AAC GGG     1037
Asn Gln Thr Phe Arg Asp Thr Tyr Ala Ala Asp Gly Gly Arg Asn Gly
            285             290             295
```

```
GTG TTT AAC TTC CCG CCC AAC GGA ACA CAC TCG TGG CCC TAC TGG AAC         1085
Val Phe Asn Phe Pro Pro Asn Gly Thr His Ser Trp Pro Tyr Trp Asn
        300                 305                 310

GAG CAG CTG GTC GCC ATG AAG GCC GAT ATC CAG CAT GTG CTC AAC GGC         1133
Glu Gln Leu Val Ala Met Lys Ala Asp Ile Gln His Val Leu Asn Gly
        315                 320                 325

GCG ACA CCC CCG GCC GCC CCT GCT GCG CCG GCC GCC TGAGCCAGCA              1179
Ala Thr Pro Pro Ala Ala Pro Ala Ala Pro Ala Ala
        330                 335             340

AGCCAGCATC GGCAGCAGCG CAACGGCCAG CG                                     1211

(2) INFORMATION FOR SEQ ID NO:3:

(i) SEQUENCE CHARACTERISTICS:
        (A) LENGTH: 340 amino acids
        (B) TYPE: amino acid
        (D) TOPOLOGY: linear (ii) MOLECULE TYPE: protein (xi) SEQUENCE DESCRIPTION: SEQ ID NO:3:

Met Thr Phe Phe Glu Gln Val Arg Arg Leu Arg Ser Ala Ala Thr Thr
 1               5                  10                  15

Leu Pro Arg Arg Val Ala Ile Ala Ala Met Gly Ala Val Leu Val Tyr
                20                  25                  30

Gly Leu Val Gly Thr Phe Gly Gly Pro Ala Thr Ala Gly Ala Phe Ser
            35                  40                  45

Arg Pro Gly Leu Pro Val Glu Tyr Leu Gln Val Pro Ser Ala Ser Met
        50                  55                  60

Gly Arg Asp Ile Lys Val Gln Phe Gln Gly Gly Pro His Ala Val
 65                 70                  75                  80

Tyr Leu Leu Asp Gly Leu Arg Ala Gln Asp Asp Tyr Asn Gly Trp Asp
                85                  90                  95

Ile Asn Thr Pro Ala Phe Glu Glu Tyr Tyr Gln Ser Gly Leu Ser Val
            100                 105                 110

Ile Met Pro Val Gly Gly Gln Ser Ser Phe Tyr Thr Asp Trp Tyr Gln
        115                 120                 125

Pro Ser Gln Ser Asn Gly Gln Asn Tyr Thr Tyr Lys Trp Glu Thr Phe
    130                 135                 140

Leu Thr Arg Glu Met Pro Ala Trp Leu Gln Ala Asn Lys Gly Val Ser
145                 150                 155                 160

Pro Thr Gly Asn Ala Ala Val Gly Leu Ser Met Ser Gly Gly Ser Ala
                165                 170                 175

Leu Ile Leu Ala Ala Tyr Tyr Pro Gln Gln Phe Pro Tyr Ala Ala Ser
            180                 185                 190

Leu Ser Gly Phe Leu Asn Pro Ser Glu Gly Trp Trp Pro Thr Leu Ile
        195                 200                 205

Gly Leu Ala Met Asn Asp Ser Gly Gly Tyr Asn Ala Asn Ser Met Trp
    210                 215                 220

Gly Pro Ser Ser Asp Pro Ala Trp Lys Arg Asn Asp Pro Met Val Gln
225                 230                 235                 240

Ile Pro Arg Leu Val Ala Asn Asn Thr Arg Ile Trp Val Tyr Cys Gly
                245                 250                 255

Asn Gly Thr Pro Ser Asp Leu Gly Gly Asp Asn Ile Pro Ala Lys Phe
            260                 265                 270

Leu Glu Gly Leu Thr Leu Arg Thr Asn Gln Thr Phe Arg Asp Thr Tyr
        275                 280                 285
```

```
Ala Ala Asp Gly Gly Arg Asn Gly Val Phe Asn Phe Pro Pro Asn Gly
    290                 295                 300

Thr His Ser Trp Pro Tyr Trp Asn Glu Gln Leu Val Ala Met Lys Ala
305                 310                 315                 320

Asp Ile Gln His Val Leu Asn Gly Ala Thr Pro Pro Ala Ala Pro Ala
                325                 330                 335

Ala Pro Ala Ala
        340
```

(2) INFORMATION FOR SEQ ID NO:4:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:4:

```
Ser Gln Ser Asn Gly Gln Asn Tyr
1               5
```

(2) INFORMATION FOR SEQ ID NO:5:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:5:

```
Pro Met Val Gln Ile Pro Arg Leu Val Ala
1               5                   10
```

(2) INFORMATION FOR SEQ ID NO:6:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:6:

```
Gly Leu Thr Leu Arg Thr Asn Gln Thr Phe Arg Asp Thr Tyr Ala Ala
1               5                   10                  15

Asp Gly Gly Arg Asn Gly
                20
```

(2) INFORMATION FOR SEQ ID NO:7:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:7:

```
Pro Pro Ala Ala Pro Ala Ala Pro Ala Ala
1               5                   10
```

(2) INFORMATION FOR SEQ ID NO:8:

(i) SEQUENCE CHARACTERISTICS:
        (A) LENGTH: 14 amino acids (B) TYPE: amino acid
            (D) TOPOLOGY: linear (ii) MOLECULE TYPE: peptide (xi) SEQUENCE DESCRIPTION: SEQ ID NO:8:

Phe Ser Arg Pro Gly Leu Pro Val Glu Tyr Leu Gln Val Pro
1               5                   10

(2) INFORMATION FOR SEQ ID NO:9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

CGGCTGGGAY ATCAACACCC CGGC                                              24

(2) INFORMATION FOR SEQ ID NO:10:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

GCCTGCGGCA AGGCCGGTTG CCAG                                              24

(2) INFORMATION FOR SEQ ID NO:11:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

GCCTGCGGTA AGGCTGGCTG CCAG                                              24

(2) INFORMATION FOR SEQ ID NO:12:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

GCCTGCGGCA AGGCCGGCTG CACG                                              24

(2) INFORMATION FOR SEQ ID NO:13:

(i) SEQUENCE CHARACTERISTICS:
            (A) LENGTH: 8 amino acids
            (B) TYPE: amino acid
            (D) TOPOLOGY: linear (ii) MOLECULE TYPE: peptide -continued (xi) SEQUENCE DESCRIPTION: SEQ ID NO:13:

Gly Trp Asp Ile Asn Thr Pro Ala
1               5

(2) INFORMATION FOR SEQ ID NO:14:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:14:

Ala Cys Gly Lys Ala Gly Cys Gln
1               5

(2) INFORMATION FOR SEQ ID NO:15:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:15:

Ala Cys Gly Lys Ala Gly Cys Thr
1               5

(2) INFORMATION FOR SEQ ID NO:16:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:16:

Asp Gly Leu Arg Ala Gln Asp Asp Tyr Asn Gly Trp Asp Ile Asn Thr
1               5                   10                  15

Pro Ala Phe Glu
            20

(2) INFORMATION FOR SEQ ID NO:17:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:17:

Thr Asp Trp Tyr Gln Pro Ser Gln Ser Asn Gly Gln Asn Tyr Thr Tyr
1               5                   10                  15

Lys Trp Glu Thr
            20

(2) INFORMATION FOR SEQ ID NO:18:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:18:

Ala Asn Ser Met Trp Gly Pro Ser Ser Asp Pro Ala Trp Lys Arg Asn
1               5                   10                  15

Asp Pro Met Val
            20

(2) INFORMATION FOR SEQ ID NO:19:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:19:

Arg Ile Trp Val Tyr Cys Gly Asn Gly Thr Pro Ser Asp Leu Gly Gly
1               5                   10                  15

Asp Asn Ile Pro
            20

(2) INFORMATION FOR SEQ ID NO:20:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:20:

Asn Gln Thr Phe Arg Asp Thr Tyr Ala Ala Asp Gly Gly Arg Asn Gly
1               5                   10                  15

Val Phe Asn Phe
            20

(2) INFORMATION FOR SEQ ID NO:21:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:21:

Gly Val Phe Asn Phe Pro Pro Asn Gly Thr His Ser Trp Pro Tyr Trp
1               5                   10                  15

Asn Glu Gln Leu
            20

(2) INFORMATION FOR SEQ ID NO:22:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:22:

Asp Ile Gln His Val Leu Asn Gly Ala Thr Pro Pro Ala Ala Pro Ala
1               5                   10                  15

Ala Pro Ala Ala
            20

(2) INFORMATION FOR SEQ ID NO:23:

(i) SEQUENCE CHARACTERISTICS:
        (A) LENGTH: 1462 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:23:

```
TGACCGGCAC CGCGATACGT TGCGGCAGGC ATCTGGGCTG GCGGTGGTTC GCCGCTCCGA      60
AGCCGTCGAA CACCATCGCC AGCGCGGCCC GGCCCGCCAC CGGGAGTGAG GGGCAATGAG     120
CGCGGGGCA ATACTGACAG CAAGATCACA ATTGAGCCGG CACATGCGTC GACACATGCC      180
CAGACACTGC GGAAATGCCA CCTTCAGGCC GTCGCGTCGG TCCCGAATTG GCCGTGAACG     240
ACCGCCGGAT AAGGGTTTCG GCGGTGCGCT TGATGCGGGT GGACGCCCGA AGTTGTGGTT     300
GACTACACGA GCACTGCCGG GCCCAGCGCC TGCAGTCTGA CCTAATTCAG GATGCGCCCA     360
AACATGCATG GATGCGTTGA GATGAGGATG AGGGAAGCAA GAATGCAGCT TGTTGACAGG     420
GTTCGTGGCG CCGTCACGGG TATGTCGCGT CGACTCGTGG TCGGGCCGT CGGCGCGGCC      480
CTAGTGTCGG GTCTGGTCGG CGCCGTCGGT GGCACGGCGA CCGCGGGGC ATTTTCCCGG      540
CCGGGCTTGC CGGTGGAGTA CCTGCAGGTG CCGTCGCCGT CGATGGGCCG TGACATCAAG     600
GTCCAATTCC AAAGTGGTGG TGCCAACTCG CCCGCCCTGT ACCTGCTCGA CGGCCTGCGC     660
GCGCAGGACG ACTTCAGCGG CTGGGACATC AACACCCCGG CGTTCGAGTG GTACGACCAG     720
TCGGGCCTGT CGGTGGTCAT GCCGGTGGGT GGCCAGTCAA GCTTCTACTC CGACTGGTAC     780
CAGCCCGCCT GCGGCAAGGC CGGTTGCCAG ACTTACAAGT GGGAGACCTT CCTGACCAGC     840
GAGCTGCCGG GGTGGCTGCA GGCCAACAGG CACGTCAAGC CCACCGGAAG CGCCGTCGTC     900
GGTCTTTCGA TGGCTGCTTC TTCGGCGCTG ACGCTGGCGA TCTATCACCC CCAGCAGTTC     960
GTCTACGCGG GAGCGATGTC GGGCCTGTTG GACCCCTCCC AGGCGATGGG TCCCACCCTG    1020
ATCGGCCTGG CGATGGGTGA CGCTGGCGGC TACAAGGCCT CCGACATGTG GGGCCCGAAG    1080
GAGGACCCGG CGTGGCAGCG CAACGACCCG CTGTTGAACG TCGGGAAGCT GATCGCCAAC    1140
AACACCCGCG TCTGGGTGTA CTGCGGCAAC GGCAAGCCGT CGGATCTGGG TGGCAACAAC    1200
CTGCCGGCCA AGTTCCTCGA GGGCTTCGTG CGGACCAGCA ACATCAAGTT CCAAGACGCC    1260
TACAACGCCG GTGGCGGCCA CAACGGCGTG TTCGACTTCC CGGACAGCGG TACGCACAGC    1320
TGGGAGTACT GGGGCGCGCA GCTCAACGCT ATGAAGCCCG ACCTGCAACG GGCACTGGGT    1380
GCCACGCCCA ACACCGGGCC CGCGCCCCAG GGCGCCTAGC TCCGAACAGA CACAACATCT    1440
AGCNNCGGTG ACCCTTGTGG NN                                            1462
```

(2) INFORMATION FOR SEQ ID NO:24:

(i) SEQUENCE CHARACTERISTICS:
        (A) LENGTH: 1091 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium bovis (xi) SEQUENCE DESCRIPTION: SEQ ID NO:24:

```
ACGACTTTCG CCCGAATCGA CATTTGGCCT CCACACACGG TATGTTCTGG CCCGAGCACA      60
CGACGACATA CAGGACAAAG GGGCACAGGT ATGACAGACG TGAGCCGAAA GATTCGAGCT     120
TGGGGACGCC GATTGATGAT CGGCACGGCA GCGGCTGTAG TCCTTCCGGG CCTGGTGGGG     180
CTTGCCGGCG GAGCGGCAAC CGCGGGCGCG TTCTCCCGGC CGGGGCTGCC GGTCGAGTAC     240
CTGCAGGTGC CGTCGCCGTC GATGGGCCGC GACATCAAGG TTCAGTTCCA GAGCGGTGGG     300
AACAACTCAC CTGCGGTTTA TCTGCTCGAC GGCCTGCGCG CCCAAGACGA CTACAACGGC     360
TGGGATATCA ACACCCCGGC GTTCGAGTGG TACTACCAGT CGGGACTGTC GATAGTCATG     420
CCGGTCGGCG GGCAGTCCAG CTTCTACAGC GACTGGTACA GCCCGGCCTG CGGTAAGGCT     480
GGCTGCCAGA CTTACAAGTG GGAAACCCTC CTGACCAGCG AGCTGCCGCA ATGGTTGTCC     540
GCCAACAGGG CCGTGAAGCC CACCGGCAGC GCTGCAATCG GCTTGTCGAT GGCCGGCTCG     600
TCGGCAATGA TCTTGGCCGC CTACCACCCC CAGCAGTTCA TCTACGCCGG CTCGCTGTCG     660
GCCCTGCTGG ACCCCTCTCA GGGGATGGGC CTGATCGGCC TCGCGATGGG TGACGCCGGC     720
GGTTACAAGG CCGCAGACAT GTGGGGTCCC TCGAGTGACC CGGCATGGGA GCGCAACGAC     780
CCTACGCAGC AGATCCCCAA GCTGGTCGCA AACAACACCC GGCTATGGGT TTATTGCGGG     840
AACGGCACCC CGAACGAGTT GGGCGGTGCC AACATACCCG CCGAGTTCTT GGAGAACTTC     900
GTTCGTAGCA GCAACCTGAA GTTCCAGGAT GCGTACAAGC CCGCGGGCGG GCACAACGCC     960
GTGTTCAACT TCCCGCCCAA CGGCACGCAC AGCTGGGAGT ACTGGGCGC TCAGCTCAAC     1020
GCCATGAAGG GTGACCTGCA GAGTTCGTTA GGCGCCGGCT GACGGGATCA ACCGAAGGTT    1080
GCTTACCCGT C                                                         1091
```

(2) INFORMATION FOR SEQ ID NO:25:

(i) SEQUENCE CHARACTERISTICS:
        (A) LENGTH: 1335 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium kansasii (vii) IMMEDIATE SOURCE:
        (B) CLONE: Antigen 85B from M. kansasii (xi) SEQUENCE DESCRIPTION: SEQ ID NO:25:

```
GTTAACTATT CTTTGTACCG CTCCCCGCCT GCCGCCTTCT GCCCTGCTCC GGGTGCATAG      60
CACCCGTTTG CGCTCCGGAT TATCCGGGCC GCAACGGGGC AACGGGGGAA GCGGGTGAGT     120
CCGTCGCCGA CTCGCATAGC ACCGTTGCTG TGTTGGCGGG GGTAACCGAT ATCGAAATGG     180
AATGACTTCG CGTCCCGATC GACATTTGCC CTACTCACAC GGTAAGTTCT GCCGGGAGCA     240
CGCGAGCACA TACGGACAAG GGGCAGGGTA TGACAGACGT GAGCGGGAAG ATTCGGGCGT     300
GGGGCCGACG CCTTCTGGTC GGCGCGGCCG CTGCTGCGGC CCTTCCTGGC CTGGTCGGAC     360
TCGCCGGCGG AGCGGCGACC GCGGGAGCGT TCTCCCGTCC CGGCCTGCCG GTGGAGTACC     420
TCCAGGTGCC GTCGGCTGCG ATGGGTCGCA GTATCAAGGT TCAATTCCAA AGTGGCGGGG     480
ACAACTCGCG GCGGTGTAC CTGCTCGACG GTCTCCGCGC TCAAGACGAC TACAACGGCT     540
GGGACATCAA CACCCCGGCC TTCGAGTGGT ACTACCAATC GGGCCTGTCG GTCATCATGC     600
```

```
CGGTCGGCGG ACAGTCCAGT TTCTACAGTG ACTGGTACAG CCCGGCCTGC GGCAAGGCCG      660

GCTGCACGAC CTACAAGTGG GAGACCTTCC TGACCAGCGA GCTGCCGCAA TGGCTGTCCG      720

CGAACCGGAG TGTCAAGCCC ACCGGAAGCG CCGCGGTCGG CATCTCGATG GCCGGCTTGT      780

CGGCCCTGAT CCTGTCCGTC TACCACCCGC AGCAGTTCAT CTACGCGGGT TCGTTGTCGG      840

CCCTGATGGA CCCCTCCCAG GGGATGGGGC CGTCTCTGAT CGGCTTGGCG ATGGGTGACG      900

CCGGTGGTTA CAAGGCCTCG GACATGTGGG GACCCTCGAG TGACCCAGCC TGGCAGCGTA      960

ACGACCCGTC GCTGCACATT CCGGAGCTGG TCGCCAACAA CACCCGCCTG TGGATCTACT     1020

GCGGCAACGG CACCCCGTCC GAGTTGGGCG GTGCCAATGT TCCGGCCGAA TTCCTGGAGA     1080

ACTTCGTTCG CAGCAGCAAC CTGAAATTCC AGGACGCCTA CAACGCCGCG GGCGGGCGGC     1140

CACAACGCCG TGTTCAATTT GGACGCCAAC GGAACGCACA GCTGGGAGTA CTGGGCGCG      1200

CAGCTCAACG CCATGAAGGG TGACCTGCAG GCCAGCCTGG GCGCCCGCTG ATCGCGCAAC     1260

GGTTGCCGCT ACTGGGCTTG ACGGCAAGAC GCCGTCAAGC CAGTAGTGTG TTCGGCACCT     1320

TGAACGCTGG TCCGC                                                     1335
```

(2) INFORMATION FOR SEQ ID NO:26:

(i) SEQUENCE CHARACTERISTICS:
        (A) LENGTH: 1178 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium tuberculosis (vii) IMMEDIATE SOURCE:
        (B) CLONE: Antigen 85C from M. tuberculosis (xi) SEQUENCE DESCRIPTION: SEQ ID NO:26:

```
AGGTGTCCGG GCCGACGCTG AATCGTTAGC CAACCGCGAT CTCGCGCTGC GGCCACGACA       60

TTCGAACTGA GCGTCCTCGG TGTGTTTCAC TCGCCCAGAA CAGATTCGAC CGCGTCGTGC      120

GCAGATGAGA GTTGGGATTG GTAGTAGCTA TGACGTTCTT CGAACAGGTG CGAAGGTTGC      180

GGAGCGCAGC GACAACCCTG CCGCGCCGCG TGGCTATCGC GGCTATGGGG GCTGTCCTGG      240

TTTACGGTCT GGTCGGTACC TTCGGCGGGC CGGCCACCGC GGGCGCATTC TCTAGGCCCG      300

GTCTTCCAGT GGAATATCTG CAGGTGCCAT CCGCGTCGAT GGGCCGCGAC ATCAAGGTCC      360

AGTTCCAGGG CGGCGGACCG CACGCGGTCT ACCTGCTCGA CGGTCTGCGG GCCCAGGATG      420

ACTACAACGG CTGGGACATC AACACCCCGG CCTTCGAGGA GTACTACCAG TCAGGGTTGT      480

CGGTGATCAT GCCCGTGGGC GGCCAATCCA GTTTCTACAC CGACTGGTAT CAGCCCTCGC      540

AGAGCAACGG CCAGAACTAC ACCTACAAGT GGGAGACCTT CCTTACCAGA GAGATGCCCG      600

CCTGGCTACA GGCCAACAAG GGCGTGTCCC CGACAGGCAA CGCGGCGGTG GGTCTTTCGA      660

TGTCGGGCGG TTCCGCGCTG ATCCTGGCCG CGTACTACCC GCAGCAGTTC CCGTACGCCG      720

CGTCGTTGTC GGGCTTCCTC AACCCGTCCG AGGGCTGGTG GCCGACGCTG ATCGGCCTGG      780

CGATGAACGA CTCGGGCGGT TACAACGCCA ACAGCATGTG GGGTCCGTCC AGCGACCCGG      840

CCTGGAAGCG CAACGACCCA ATGGTTCAGA TTCCCCGCCT GGTCGCCAAC AACACCCGGA      900

TCTGGGTGTA CTGCGGTAAC GGCACACCCA GCGACCTCGG CGGCGACAAC ATACCGGCGA      960

AGTTCCTGGA AGGCCTCACC CTGCGCACCA ACCAGACCTT CCGGGACACC TACGCGGCCG     1020

ACGGTGGACG CAACGGGGTG TTTAACTTCC CGCCCAACGG AACACACTCG TGGCCCTACT     1080
```

```
GGAACGAGCA GCTGGTCGCC ATGAAGGCCG ATATCCAGCA TGTGCTCAAC GGCGCGACAC      1140

CCCCGGCCGC CCCTGCTGCG CCGGCCGCCT GAGCCAGC                              1178
```

(2) INFORMATION FOR SEQ ID NO:27:

(i) SEQUENCE CHARACTERISTICS:
        (A) LENGTH: 185 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium bovis (vii) IMMEDIATE SOURCE:
        (B) CLONE: Partial DNA sequence from M. bovis BCG strain 1173P2

(xi) SEQUENCE DESCRIPTION: SEQ ID NO:27:

CTGCTCGACG GTCTGCGGGC CCAGGATGAC TACAACGGCT GGGACATCAA CACCCCGGCC 60

TTCGAGGAGT ACTACCAGTC AGGGTTGTCG GTGATCATGC CCGTGGGCGG CCAATCCAGT 120

TTCTACACCG ACTGGTATCA GCCCTCGCAG AGCAACGGCC AGAACTACAC TTACAAGTGG 180

GAGAC 185

(2) INFORMATION FOR SEQ ID NO:28:

(i) SEQUENCE CHARACTERISTICS:
(A) LENGTH: 338 amino acids
(B) TYPE: amino acid
(D) TOPOLOGY: linear (ii) MOLECULE TYPE: protein (vi) ORIGINAL SOURCE:
(A) ORGANISM: Mycobacterium tuberculosis (vii) IMMEDIATE SOURCE:
(B) CLONE: Antigen 85A protein sequence from M. tuberculosis (xi) SEQUENCE DESCRIPTION: SEQ ID NO:28:

Met Gln Leu Val Asp Arg Val Arg Gly Ala Val Thr Gly Met Ser Arg
1 5 10 15

Arg Leu Val Val Gly Ala Val Gly Ala Ala Leu Val Ser Gly Leu Val
20 25 30

Gly Ala Val Gly Gly Thr Ala Thr Ala Gly Ala Phe Ser Arg Pro Gly
35 40 45

Leu Pro Val Glu Tyr Leu Gln Val Pro Ser Pro Ser Met Gly Arg Asp
50 55 60

Ile Lys Val Gln Phe Gln Ser Gly Gly Ala Asn Ser Pro Ala Leu Tyr
65 70 75 80

Leu Leu Asp Gly Leu Arg Ala Gln Asp Asp Phe Ser Gly Trp Asp Ile
85 90 95

Asn Thr Pro Ala Phe Glu Trp Tyr Asp Gln Ser Gly Leu Ser Val Val
100 105 110

Met Pro Val Gly Gly Gln Ser Ser Phe Tyr Ser Asp Trp Tyr Gln Pro
115 120 125

Ala Cys Gly Lys Ala Gly Cys Gln Thr Tyr Lys Trp Glu Thr Phe Leu
130 135 140

Thr Ser Glu Leu Pro Gly Trp Leu Gln Ala Asn Arg His Val Lys Pro

```
                    145                 150                 155                 160
        Thr Gly Ser Ala Val Gly Leu Ser Met Ala Ala Ser Ser Ala Leu
                        165                 170                 175
        Thr Leu Ala Ile Tyr His Pro Gln Gln Phe Val Tyr Ala Gly Ala Met
                        180                 185                 190
        Ser Gly Leu Leu Asp Pro Ser Gln Ala Met Gly Pro Thr Leu Ile Gly
                        195                 200                 205
        Leu Ala Met Gly Asp Ala Gly Gly Tyr Lys Ala Ser Asp Met Trp Gly
                        210                 215                 220
        Pro Lys Glu Asp Pro Ala Trp Gln Arg Asn Asp Pro Leu Leu Asn Val
        225                 230                 235                 240
        Gly Lys Leu Ile Ala Asn Asn Thr Arg Val Trp Val Tyr Cys Gly Asn
                        245                 250                 255
        Gly Lys Pro Ser Asp Leu Gly Gly Asn Asn Leu Pro Ala Lys Phe Leu
                        260                 265                 270
        Glu Gly Phe Val Arg Thr Ser Asn Ile Lys Phe Gln Asp Ala Tyr Asn
                        275                 280                 285
        Ala Gly Gly His Asn Gly Val Phe Asp Phe Pro Asp Ser Gly Thr
                290                 295                 300
        His Ser Trp Glu Tyr Trp Gly Ala Gln Leu Asn Ala Met Lys Pro Asp
        305                 310                 315                 320
        Leu Gln Arg Ala Leu Gly Ala Thr Pro Asn Thr Gly Pro Ala Pro Gln
                        325                 330                 335
        Gly Ala
```

(2) INFORMATION FOR SEQ ID NO:29:

(i) SEQUENCE CHARACTERISTICS:
        (A) LENGTH: 325 amino acids
        (B) TYPE: amino acid
        (D) TOPOLOGY: linear (ii) MOLECULE TYPE: protein (vi) ORIGINAL SOURCE:
        (A) ORGANISM: Mycobacterium bovis (vii) IMMEDIATE SOURCE:
        (B) CLONE: Antigen 85B protein sequence from
            alpha-antigen of M.bovis (xi) SEQUENCE DESCRIPTION: SEQ ID NO:29:

```
        Met Thr Asp Val Ser Arg Lys Ile Arg Ala Trp Gly Arg Arg Leu Met
        1               5                   10                  15
        Ile Gly Thr Ala Ala Ala Val Val Leu Pro Gly Leu Val Gly Leu Ala
                        20                  25                  30
        Gly Gly Ala Ala Thr Ala Gly Ala Phe Ser Arg Pro Gly Leu Pro Val
                        35                  40                  45
        Glu Tyr Leu Gln Val Pro Ser Pro Ser Met Gly Arg Asp Ile Lys Val
              50                  55                  60
        Gln Phe Gln Ser Gly Gly Asn Asn Ser Pro Ala Val Tyr Leu Leu Asp
        65                  70                  75                  80
        Gly Leu Arg Ala Gln Asp Asp Tyr Asn Gly Trp Asp Ile Asn Thr Pro
                        85                  90                  95
        Ala Phe Glu Trp Tyr Tyr Gln Ser Gly Leu Ser Ile Val Met Pro Val
                        100                 105                 110
        Gly Gly Gln Ser Ser Phe Tyr Ser Asp Trp Tyr Ser Pro Ala Cys Gly
                        115                 120                 125
```

```
Lys Ala Gly Cys Gln Thr Tyr Lys Trp Glu Thr Leu Leu Thr Ser Glu
    130                 135                 140
Leu Pro Gln Trp Leu Ser Ala Asn Arg Ala Val Lys Pro Thr Gly Ser
145                 150                 155                 160
Ala Ala Ile Gly Leu Ser Met Ala Gly Ser Ser Ala Met Ile Leu Ala
                165                 170                 175
Ala Tyr His Pro Gln Gln Phe Ile Tyr Ala Gly Ser Leu Ser Ala Leu
            180                 185                 190
Leu Asp Pro Ser Gln Gly Met Gly Pro Ser Leu Ile Gly Leu Ala Met
        195                 200                 205
Gly Asp Ala Gly Gly Tyr Lys Ala Ala Asp Met Trp Gly Pro Ser Ser
    210                 215                 220
Asp Pro Ala Trp Glu Arg Asn Asp Pro Thr Gln Gln Ile Pro Lys Leu
225                 230                 235                 240
Val Ala Asn Asn Thr Arg Leu Trp Val Tyr Cys Gly Asn Gly Thr Pro
                245                 250                 255
Asn Glu Leu Gly Gly Ala Asn Ile Pro Ala Glu Phe Leu Glu Asn Phe
            260                 265                 270
Val Arg Ser Ser Asn Leu Lys Phe Gln Asp Ala Tyr Lys Pro Ala Gly
        275                 280                 285
Gly His Asn Ala Val Phe Asn Phe Pro Pro Asn Gly Thr His Ser Trp
    290                 295                 300
Glu Tyr Trp Gly Ala Gln Leu Asn Ala Met Lys Gly Asp Leu Gln Ser
305                 310                 315                 320
Ser Leu Gly Ala Gly
                325

(2) INFORMATION FOR SEQ ID NO:30:

(i) SEQUENCE CHARACTERISTICS:
        (A) LENGTH: 325 amino acids
        (B) TYPE: amino acid
        (D) TOPOLOGY: linear (ii) MOLECULE TYPE: protein (vi) ORIGINAL SOURCE:
        (A) ORGANISM: Mycobacterium kansasii (vii) IMMEDIATE SOURCE:
        (B) CLONE: Partial protein sequence from antigen 85B
            from M.

-continued

```
                115                 120                 125
Lys Ala Gly Cys Thr Thr Tyr Lys Trp Glu Thr Phe Leu Thr Ser Glu
    130                 135                 140
Leu Pro Gln Trp Leu Ser Ala Asn Arg Ser Val Lys Pro Thr Gly Ser
145                 150                 155                 160
Ala Ala Val Gly Ile Ser Met Ala Gly Ser Ser Ala Leu Ile Leu Ser
                165                 170                 175
Val Tyr His Pro Gln Gln Phe Ile Tyr Ala Gly Ser Leu Ser Ala Leu
                180                 185                 190
Met Asp Pro Ser Gln Gly Met Gly Pro Ser Leu Ile Gly Leu Ala Met
            195                 200                 205
Gly Asp Ala Gly Gly Tyr Lys Ala Ser Asp Met Trp Gly Pro Ser Ser
    210                 215                 220
Asp Pro Ala Trp Gln Arg Asn Asp Pro Ser Leu His Ile Pro Glu Leu
225                 230                 235                 240
Val Ala Asn Asn Thr Arg Leu Trp Ile Tyr Cys Gly Asn Gly Thr Pro
                245                 250                 255
Ser Glu Leu Gly Gly Ala Asn Val Pro Ala Glu Phe Leu Glu Asn Phe
            260                 265                 270
Val Arg Ser Ser Asn Leu Lys Phe Gln Asp Ala Tyr Asn Ala Ala Gly
    275                 280                 285
Gly His Asn Ala Val Phe Asn Leu Asp Ala Asn Gly Thr His Ser Trp
    290                 295                 300
Glu Tyr Trp Gly Ala Gln Leu Asn Ala Met Lys Gly Asp Leu Gln Ala
305                 310                 315                 320
Ser Leu Gly Ala Arg
                325
```

(2) INFORMATION FOR SEQ ID NO:31:

(i) SEQUENCE CHARACTERISTICS:
        (A) LENGTH: 340 amino acids
        (B) TYPE: amino acid
        (D) TOPOLOGY: linear (ii) MOLECULE TYPE: protein (vi) ORIGINAL SOURCE:
        (A) ORGANISM: Mycobacterium tuberculosis (vii) IMMEDIATE SOURCE:
        (B) CLONE: Protein sequence from antigen 85C from M.
            tuberculosis (xi) SEQUENCE DESCRIPTION: SEQ ID NO:31:

```
Met Thr Phe Phe Glu Gln Val Arg Arg Leu Arg Ser Ala Ala Thr Thr
1               5                   10                  15
Leu Pro Arg Arg Val Ala Ile Ala Ala Met Gly Ala Val Leu Val Tyr
                20                  25                  30
Gly Leu Val Gly Thr Phe Gly Gly Pro Ala Thr Ala Gly Ala Phe Ser
            35                  40                  45
Arg Pro Gly Leu Pro Val Glu Tyr Leu Gln Val Pro Ser Ala Ser Met
    50                  55                  60
Gly Arg Asp Ile Lys Val Gln Phe Gln Gly Gly Pro His Ala Val
65                  70                  75                  80
Tyr Leu Leu Asp Gly Leu Arg Ala Gln Asp Asp Tyr Asn Gly Trp Asp
                85                  90                  95
Ile Asn Thr Pro Ala Phe Glu Glu Tyr Tyr Gln Ser Gly Leu Ser Val
                100                 105                 110
```

Ile Met Pro Val Gly Gly Gln Ser Ser Phe Tyr Thr Asp Trp Tyr Gln
          115                 120                 125

Pro Ser Gln Ser Asn Gly Gln Asn Tyr Thr Tyr Lys Trp Glu Thr Phe
        130                 135                 140

Leu Thr Arg Glu Met Pro Ala Trp Leu Gln Ala Asn Lys Gly Val Ser
145                 150                 155                 160

Pro Thr Gly Asn Ala Ala Val Gly Leu Ser Met Ser Gly Gly Ser Ala
                165                 170                 175

Leu Ile Leu Ala Ala Tyr Tyr Pro Gln Gln Phe Pro Tyr Ala Ala Ser
            180                 185                 190

Leu Ser Gly Phe Leu Asn Pro Ser Glu Gly Trp Trp Pro Thr Leu Ile
        195                 200                 205

Gly Leu Ala Met Asn Asp Ser Gly Gly Tyr Asn Ala Asn Ser Met Trp
    210                 215                 220

Gly Pro Ser Ser Asp Pro Ala Trp Lys Arg Asn Asp Pro Met Val Gln
225                 230                 235                 240

Ile Pro Arg Leu Val Ala Asn Asn Thr Arg Ile Trp Val Tyr Cys Gly
            245                 250                 255

Asn Gly Thr Pro Ser Asp Leu Gly Gly Asp Asn Ile Pro Ala Lys Phe
        260                 265                 270

Leu Glu Gly Leu Thr Leu Arg Thr Asn Gln Thr Phe Arg Asp Thr Tyr
    275                 280                 285

Ala Ala Asp Gly Gly Arg Asn Gly Val Phe Asn Phe Pro Pro Asn Gly
    290                 295                 300

Thr His Ser Trp Pro Tyr Trp Asn Glu Gln Leu Val Ala Met Lys Ala
305                 310                 315                 320

Asp Ile Gln His Val Leu Asn Gly Ala Thr Pro Ala Ala Pro Ala
            325                 330                 335

Ala Pro Ala Ala
        340

(2) INFORMATION FOR SEQ ID NO:32:

(i) SEQUENCE CHARACTERISTICS:
        (A) LENGTH: 57 amino acids
        (B) TYPE: amino acid
        (D) TOPOLOGY: linear (ii) MOLECULE TYPE: protein (vi) ORIGINAL SOURCE:
        (A) ORGANISM: Mycobacterium bovis (vii) IMMEDIATE SOURCE:
        (B) CLONE: Partial sequence from M. bovis BCG strain
            1173P2

(xi) SEQUENCE DESCRIPTION: SEQ ID NO:32:

Tyr Leu Leu Asp Gly Leu Arg Ala Gln Asp Asp Tyr Asn Gly Trp Asp
1               5                   10                  15

Ile Asn Thr Pro Ala Phe Glu Glu Tyr Tyr Gln Ser Gly Leu Ser Val
            20                  25                  30

Ile Met Pro Val Gly Gly Gln Ser Ser Phe Tyr Thr Asp Trp Tyr Gln
            35                  40                  45

Pro Ser Gln Ser Asn Gly Gln Asn Tyr
        50                  55

(2) INFORMATION FOR SEQ ID NO:33:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Sense P78 oligonucleotide primer (xi) SEQUENCE DESCRIPTION: SEQ ID NO:33:

CCGGAATTCA TGGGCCGTGA CATCAAG                                   27

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Antisense P79 oligonucleotide primer (xi) SEQUENCE DESCRIPTION: SEQ ID NO:34:

CCGGAATTCG GTCTCCCACT TGTAAGT                                   27

(2) INFORMATION FOR SEQ ID NO:35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: 32p-labeled oligonucleotide probe-A (xi) SEQUENCE DESCRIPTION: SEQ ID NO:35:

TCGCCCGCCC TGTACCTG                                             18

(2) INFORMATION FOR SEQ ID NO:36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Oligonucleotide probe-B (xi) SEQUENCE DESCRIPTION: SEQ ID NO:36:

TCACCTGCGG TTTATCTG                                             18

(2) INFORMATION FOR SEQ ID NO:37:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

-continued

```
   (vii) IMMEDIATE SOURCE:
          (B) CLONE: 32p-labeled oligonucleotide probe-C (xi) SEQUENCE DESCRIPTION: SEQ ID NO:37:

TCGCAGAGCA ACGGCCAGAA CTAC                                         24

(2) INFORMATION FOR SEQ ID NO:38:

(i) SEQUENCE CHARACTERISTICS:
          (A) LENGTH: 26 amino acids
          (B) TYPE: amino acid
          (D) TOPOLOGY: linear (ii) MOLECULE TYPE: protein (xi) SEQUENCE DESCRIPTION: SEQ ID NO:38:

Phe Ser Arg Pro Gly Leu Pro Val Glu Tyr Leu Gln Val Pro Ser Ala
1               5                   10                  15

Ser Met Gly Arg Asp Ile Lys Val Gln Phe
            20                  25
```